US012642867B2

(12) United States Patent
Willner et al.

(10) Patent No.: US 12,642,867 B2
(45) Date of Patent: Jun. 2, 2026

(54) CONJUGATES COMPRISING OCULAR ANGIOGENESIS GROWTH FACTOR APTAMERS AND USES THEREOF IN THE DETECTION AND TREATMENT OF OPHTHALMOLOGICAL ANGIOGENESIS INDICATIONS

(71) Applicants: Yissum Research Development Company of the Hebrew University of Jerusalem Ltd., Jerusalem (IL); Bar Ilan University, Ramat Gan (IL)

(72) Inventors: Itamar Willner, Mevasseret Zion (IL); Sharon Etery, Rishon le Tzion (IL); Yossi Mandel, Givataim (IL); Amos Markus, Petah Tikva (IL); Asaf Shoval, Raanana (IL)

(73) Assignees: YISSUM RESEARCH DEVELOPMENT COMPANY OF THE HEBREW UNIVERSITY OF JERUSALEM LTD., Jerusalem (IL); BAR ILAN UNIVERSITY, Ramat Gan (IL)

( * ) Notice: Subject to any disclaimer, the term of this patent is extended or adjusted under 35 U.S.C. 154(b) by 1078 days.

(21) Appl. No.: 16/489,221

(22) PCT Filed: Feb. 28, 2018

(86) PCT No.: PCT/IL2018/050228
§ 371 (c)(1),
(2) Date: Aug. 27, 2019

(87) PCT Pub. No.: WO2018/158771
PCT Pub. Date: Sep. 7, 2018

(65) Prior Publication Data
US 2020/0000934 A1 Jan. 2, 2020

Related U.S. Application Data

(60) Provisional application No. 62/467,154, filed on Mar. 5, 2017, provisional application No. 62/464,396, filed on Feb. 28, 2017.

(51) Int. Cl.
*A61K 9/00* (2006.01)
*A61K 31/711* (2006.01)
(Continued)

(52) U.S. Cl.
CPC ........ *A61K 47/6929* (2017.08); *A61K 9/0048* (2013.01); *A61K 31/711* (2013.01);
(Continued)

(58) Field of Classification Search
CPC .................................................. A61K 47/6929
See application file for complete search history.

(56) References Cited

U.S. PATENT DOCUMENTS 7,641,915 B2 1/2010 Chen et al.
8,138,005 B2 3/2012 Jang et al.

FOREIGN PATENT DOCUMENTS

CN 104964960 A 10/2015
CN 106290873 A 1/2017
(Continued)

OTHER PUBLICATIONS

Eugene, Pegaptanib, a targed anti-VEGF aptamer for ocular vascular disease, Nature Reviews, 2006, 5, 123-132 (Year: 2006).*
(Continued)

*Primary Examiner* — Paul W Dickinson
(74) *Attorney, Agent, or Firm* — FISHERBROYLES, LLP; Roger L. Browdy

(57) ABSTRACT

Provided is an antiangiogenic agent in the form of a vehicle, e.g., a nanoparticle associated (directly or indirectly) with at least one ocular angiogenesis growth factor aptamer,
(Continued)

wherein said association labile to interaction between the aptamer and an ocular angiogenesis growth factor.

10 Claims, 10 Drawing Sheets

Specification includes a Sequence Listing.

(51) Int. Cl.
| | | |
|---|---|---|
| *A61K 47/69* | (2017.01) | |
| *A61K 49/00* | (2006.01) | |
| *A61P 27/02* | (2006.01) | |
| *C12N 15/115* | (2010.01) | |

(52) U.S. Cl.
CPC ...... *A61K 47/6923* (2017.08); *A61K 49/0054* (2013.01); *A61K 49/0093* (2013.01); *A61P 27/02* (2018.01); *C12N 15/115* (2013.01); *C12N 2310/16* (2013.01); *C12N 2310/3517* (2013.01)

(56) References Cited

FOREIGN PATENT DOCUMENTS

| | | |
|---|---|---|
| KR | 10-1009938 B1 | 1/2011 |
| WO | 2005/020972 A2 | 3/2005 |
| WO | 2008/147438 A2 | 12/2008 |
| WO | 2009/155504 A2 | 12/2009 |
| WO | 2012/105610 A1 | 8/2012 |
| WO | 2017/184427 A1 | 10/2017 |

OTHER PUBLICATIONS

Eugene et al, Pegaptanib, a targeted anti-VEGF aptamer for ocular vascular disease, Nature Reviews, 5, 2006, 123-132. (Year: 2006).*

Bruno, "A Review of Therapeutic Aptamer Conjugates with Emphasis on New Approaches", Pharmaceuticals, 2013, vol. 6, pp. 340-357.

Chen et al., "ATP-Responsive Aptamer-Based Metal-Organic Framework Nanoparticles (NMOFs) for the Controlled Release of Loads and Drugs", Adv. Funct. Mater., 2017, vol. 27, pp. 1702102 (9 pages).

Drolet et al., "Fit for the Eye: Aptamers in Ocular Disorders", Nucleic Acid Therapeutics, vol. 26, No. 3, pp. 127-146, (2016).

Freeman et al., "Optical Aptasensors for the Analysis of the Vascular Endothelial Growth Factor (VEGF)", Anal. Chem., 2012, vol. 84, pp. 6192-6198.

Lu et al., "Metal-Enhanced Fluorescence-Based Core-Shell Ag@SiO2 Nanoflares for Affinity Biosensing via Target-Induced Structure Switching of Aptamer", ACS Appl. Mater. Interfaces, 2014, vol. 6, pp. 1944-1950.

Miao et al., "Recent advances in carbon nanodots: synthesis, properties and biomedical applications", Nanoscale, 2015, vol. 7, pp. 1586-1595.

Ng et al., "Pegaptanib, a targeted anti-VEGF aptamer for ocular vascular disease", Nature Reviews: Drug Discovery, vol. 5, pp. 123-132, (2006).

Nonaka et al., "Screening and Improvement of an Anti-VEGF DNA Aptamer", Molecules, 2010, vol. 15, pp. 215-225.

Ryou et al., "Gold nanoparticle-assisted delivery of small, highly structured RNA into the nuclei of human cells", Biochemical and Biophysical Research Communications, vol. 416, pp. 178-183, (2011).

Shukoor et al., "Aptamer-Nanoparticle Assembly for Logic-Based Detection", ACS Appl. Mater. Interfaces, 2012, vol. 4, pp. 3007-3011.

Zheng et al., "Aptamer Nano-flares for Molecular Detection in Living Cells", Nano Letters, 2009, vol. 9, No. 9, pp. 3258-3261.

Janagam et al., "Nanoparticles for drug delivery to the anterior segment of the eye", Adv Drug Deliv Rev., 2017, 122; 31-64.

Xu, et al., Aptamer carbon nanodot sandwich used for fluorescent detection of protein, Analyst, 137:5483-5486 (2012).

FREEMAN et l., "Optical Aptasensors for the Analysis of the Vascular Endothelial Growth Factor (VEGF)", Anal. Chem., 2012, vol. 84, Supporting Information (ac3011473_si_001.pdf).

* cited by examiner

1

CONJUGATES COMPRISING OCULAR ANGIOGENESIS GROWTH FACTOR APTAMERS AND USES THEREOF IN THE DETECTION AND TREATMENT OF OPHTHALMOLOGICAL ANGIOGENESIS INDICATIONS

SEQUENCE LISTING

The Sequence Listing submitted in text format (.txt) filed on Aug. 27, 2019, named "SequenceListing.txt", created on Aug. 19, 2019 (1.14 KB), is incorporated herein by reference.

TECHNOLOGICAL FIELD

The present invention relates to conjugates comprising at least one ocular angiogenesis growth factor aptamer and uses thereof in the detection and treatment of ophthalmological indications.

BACKGROUND

Age related macular degeneration (AMD) and Diabetic retinopathy (DR) as well as some other ophthalmological conditions are characterized by pathological retinal blood vessels development causing retinal edema and loss of vision. AMD is the leading cause of vision loss in people over 50 in the Western world with increased incidence anticipated with the gradually increasing aging population.

The US National Eye Institute (NEI) estimates that by 2020, 3 million Americans will be blinded by this disease. There are two types of AMD: wet (neovascular) AMD and dry AMD. For both types of AMD there is currently no optimal treatment or cure; however, wet AMD is currently treated with repeated intraocular injections of anti-VEGF agents, which have been proven to slow the disease progression.

Another major cause of blindness is retinopathy caused by diabetes mellitus, which is the leading cause of new onset blindness for people aged 20-74 years with about one-third of patients with diabetes aged 40 and older having diabetic retinopathy.

Similar statistics are reported in European cohort. Globally, diabetes affects more than 360 million individuals and is expected to affect more than half a billion by 2030 and about 170 million individuals will show signs of retinopathy. Other sources estimate that more than 90 million individuals have diabetic retinopathy, with about 21 million having DME and 17 million having PDR, in developed countries.

Both, AMD and DR are caused by growth of diseased blood vessels, which cause leakage of fluid into the retina, causing retinal edema and severe decrease in visual acuity and contrast sensitivity. The growth of these pathological blood vessels is triggered by high levels of intraocular vascular endothelial growth factor (VEGF).

In AMD, and in some types of DR, repeated injections of anti VEGF agents are the only available treatment and have been found to slow disease progression, albeit not completely cure. Notwithstanding, repeated (monthly) intraocular injections of anti-VEGF agents are routinely administered to the patients in clinic or operating room and, unfortunately, carry several major risks to the eye, such as severe infection, cataract and others. Moreover, intraocular injections can only be administered by highly experienced ophthalmologists and para-medical personnel, who are not readily available in developing countries.

Another major drawback of the current anti-VEGF treatment is that treatment is standardized and is not titrated by the levels of VEGF in the eye. Customization of treatment can be determined by measuring VEGF levels in the eye. Unfortunately, currently there is no technology enabling non-invasive measurement of intraocular VEGF levels.

REFERENCES

[1] J. G. Bruno. *Pharmaceuticals* 2013, 6, 340-357.
[2] Y. Nonaka et al. *Molecules* 2010, 15, 215-225.
[3] W. M. Eugene et al. *Nature Reviews Drug Discovery* 2006, 5, 123-132.

GENERAL DESCRIPTION

Current ophthalmic anti-VEGF therapy is administered by repeated intraocular injections. There is an ongoing debate regarding optimized treatment protocols, which is either standardized or modified according to anatomical or functional repeated evaluation. The present invention proposed a "sense and treat" approach, where the efficacy and the need for treatment are monitored by optically measuring VEGF levels in the eye. The agents or nanostructure complexes of the invention are used to enhance drug tissue permeability upon topical administration, therefore eliminating the need for repeated injections into the eye.

Along with its benefits to patients, the novel methodology also has economic benefits. Estimations of cost of anti VEGF treatment is very high and expected to grow with the increasing age of population. The cost of anti VEGF treatment is estimated as over €1.2 B in India, €1 B in UK and €3.3 B in Germany Topical administration of anti VEGF by the patient can dramatically reduce adverse effect prevalence, treatment cost and enhance accessibility of treatment to diabetic patients, as there is no need for patients to visit their physicians' for treatment. This treatment can revolutionize ophthalmic anti VEGF treatment by both providing simple topical administration drug, eliminating the need for intraocular injection, while utilizing the sensing capabilities of the aptasensor for monitoring disease activity and the need for treatment.

Importantly, the technology is also suitable for improving treatment in ophthalmic complication of diabetic retinopathy, as anti-VEGF agents are also extensively used for both diabetic macular edema (DME) and proliferative diabetic retinopathy (PDR).

The approach at the heart of the technology is based on the construction of an aptamer-delivery system and a sensor system for measuring ocular VEGF or other growth factors, involved in the pathogenesis of blood vessels in the eye. The system is based on an aptasensor composed of anti-VEGF aptamer coupled with a quencher which are mounted on fluorescent carrier, such as carbon quantum dots (C-dots). In the complex, the C-dots inherent fluorescence is quenched by the quencher-aptamer complex. However, when the complex "meets" free VEGF in the eye, the quencher-aptamer complex is released from the C-dots, switching "on" the label fluorescence. The fluorescence can then be read by a customized ocular fluorimeter, providing the sensing capability of the intraocular free VEGF. In cases where VEGF is detected at high levels in the eye, the same aptamer without the fluorophore label is applied for blocking VEGF activity.

Thus, in fact, the invention provides a tool that may be used as a therapeutic tool, a diagnostic tool or a sense-and-treat tool which combines diagnosis and optional treatment in case necessary.

In one of its aspects, the invention provides an antiangiogenic agent in the form of a vehicle, e.g., a nanoparticle associated (directly or indirectly) with at least one ocular angiogenesis growth factor aptamer (herein "aptamer"), wherein said association having lability to interaction between the aptamer and an ocular angiogenesis growth factor (herein "OAGF") (namely upon such interaction dissociation of the vehicle from the aptamer occurs).

As used herein, the "antiangiogenic agent", which comprises the vehicle and the aptamer, functions as an angiogenesis inhibitor, namely an agent which inhibits the growth of new blood vessels. According to the present invention, the antiangiogenic agent targets the ocular angiogenesis growth factor or similar growth factor pathway. By binding to the OAGF, the agent of the invention inhibits endothelial cell proliferation, migration, tube formation, or any combination thereof, through the induction of an immune response, stasis, cell death, or necrosis.

As used herein, the term "vehicle", encompasses any type of bio-acceptable material that can be used or can act as a carrier or a delivery unit for holding the aptamer. In some embodiments, the vehicle is in the form of a particulate material. In some embodiments, the vehicle is a fluorophore material, which is optionally in particulate form.

The particulate material, being a fluorophore or not, may be of any size and shape. Yet, in some embodiments, the particulate material is composed of particles that at least a portion thereof is in the nanometer scale. In some embodiments, the particulate material is in the form of nanoparticles.

In some embodiments, the vehicle is configured to carry the aptamer to the target site or tissue and assist in its penetration into the eye. Thereby, the vehicle enables controlled release or programed release of the aptamer. The vehicle, as will be further elaborated on further below, also enables measuring the amount of aptamer in the eye.

Where the vehicle is in the form of a nanoparticle, said nanoparticle is of a material suitable for ocular application. Such materials may be selected from carbon quantum dots (C-dots), graphene oxide nanoparticles, DNA based nanoparticles, carbon nitride nanoparticles, metal organic framework nanoparticles, polymeric nanoparticles, polysaccharide nanoparticles and any combinations thereof. Each vehicle, e.g., nanoparticle may be associated with one or more aptamer units. In some embodiments, the aptamer is not contained within the vehicle but rather associated to its surface.

In some embodiments, the aptamer is directly associated to the vehicle, e.g., a nanoparticle. The association may be adsorption of the aptamer directly onto the surface of the vehicle, or by any labile bond to a group or an atom or a group of atoms extending from the surface of the vehicle.

In other embodiments, the aptamer is indirectly associated to the vehicle, e.g., nanoparticle. The indirect association may be by a linker moiety or a spacer moiety that, at one end, binds or associates to the vehicle and, at another end, binds or associates to the aptamer. The association at both ends of the linker moiety or spacer moiety is selected to permit cleavage of the aptamer from the linker or spacer moiety upon association with the OAGF. In other words, to allow cleavage or dissociation of a bond or association between the aptamer and the linker or spacer moiety, at least the bond between the moiety and the aptamer must be configured to allow the linkage between the aptamer and the vehicle to break or dissociate or become cleaved. In such a case, dissociation of the bond between the linker or spacer moiety and the vehicle need not be labile.

In some embodiments, the linker or spacer moiety is a nucleotide sequence (e.g., DNA) that is covalently bound or associated to the vehicle, e.g., nanoparticles, and which can be hybridized to the aptamer sequence. This complimentary nucleotide sequence is selected based on the sequence of the aptamer, such that at least a region of the aptamer or an extension of the aptamer may be hybridized to the nucleotide sequence. The at least a region is of at least nine nucleic acid. In other words, the linking between the aptamer unit and the vehicle is by at least 9 base-pairs.

In some embodiments, the vehicle, e.g., nanoparticle is conjugated or modified to be associated to a nucleic acid sequence, e.g., an oligonucleotide, such as a single-stranded DNA, capable of specifically hybridizing with a complementary region(s) of the aptamer. The complementary region of the aptamer is a 9-base region which may be contiguous to which a complementary 9-base region of the nucleic acid sequence on the vehicle hybridizes. For achieving sufficient loading of the vehicle with the aptamer units, each vehicle, e.g., each nanoparticle has a plurality of oligonucleotides attached to it. Each nanoparticle-oligonucleotide conjugate can bind to an aptamer having the complementary sequence.

The vehicle oligonucleotides may be obtained by any method of making oligonucleotides of a predetermined sequence. See, e.g., Sambrook et al., *Molecular Cloning: A Laboratory Manual* (2nd ed. 1989) and F. Eckstein (ed.) *Oligonucleotides and Analogues,* 1st Ed. (Oxford University Press, New York, 1991). Solid-phase synthesis methods may also be used.

In some embodiments, the linker or spacer moiety is a nucleic acid sequence. In some embodiments, the linker or spacer moiety is a single-stranded DNA sequence.

In some embodiments, the linker or spacer moiety is a single stranded nucleic acid sequence comprising, e.g., the sequence 5'-TCTACCCGGCCC-3' (SEQ ID NO: 1). In some embodiments, the vehicle is associated with SEQ ID NO: 1, directly or indirectly. In some embodiments, SEQ ID NO: 1 is associated with a surface region of the vehicle, e.g., nanoparticle, such that at least a portion of the sequence is available for hybridization to a complementary region of the aptamer. As indicated above, the hybridization of the sequence to the aptamer is via at least 9 bases along both sequences, the at least 9 bases need not be consecutive. In other embodiments, the SEQ ID NO: 1 is associated to the vehicle, nanoparticle, via a functional groups that permits covalent association with the vehicle. Such functional groups may be selected based on functionalities available on the vehicle, e.g., nanoparticle. Functional groups that may be attached to the sequence, e.g., SEQ ID NO: 1, include amine groups, alcohol groups, carboxyl groups and others.

In some embodiments, the sequence is substituted with an extension groups comprising between 1 and 10 atoms, e.g., carbon atoms, with an end groups being selected from amine groups, alcohol groups, carboxyl groups and others. In some embodiments, the end group is an amine group. Thus, according to an exemplary embodiment of the invention, SEQ ID NO: 1 is substituted/functionalized to provide the sequence 5'-NH$_2$—(CH$_2$)$_n$-TCTACCCGGCCC-3' (SEQ ID NO:2), wherein n is an integer between 1 and 10. The amine end group, as an example, may be replaced with any other functional groups capable of forming covalent association with a functional group on the vehicle, e.g., nanoparticle. Where the sequence is substituted with an amine group, as exemplified, the vehicle, nanoparticle, may be substituted or modified to include carboxyl functionalities. In SEQ ID NO: 2, n may be between 1 and 9, 1 and 8, 1 and 7, 1 and 6, 1 and 5, 1 and 4, 1 and 3, 2 and 9, 2 and 8, 2 and 7, 2 and 6, 2 and 5, 2 and 4, 3 and 9, 3 and 8, 3 and 7, 3 and 5, 4 and 9, 4 and 8, 4 and 7, 4 and 6, 5 and 9, 5 and 8, 5 and 7, 6 and 9, 6 and 8, or n is 1, 2, 3, 4, 5, 6, 7, 8, 9, or 10. In some embodiments, the sequence is SEQ ID NO:2, wherein n=6, or n=2. In some embodiments, the vehicle is a nanoparticle, e.g., C-dot, associated with the sequence 5'-NH$_2$—(CH$_2$)$_6$-TCTACCCGGCCC-3' (SEQ ID NO:2), to permit association with the aptamer via interaction between nine or more of the nucleic acids in the aptamer sequence and nine or more of the nucleic acids in the vehicle associated sequence.

It is thus understood that the association of the aptamer to the vehicle may be in a variety of forms and may be achieved by any one of a variety of chemical methods. Non-limiting examples of such associations are presented in FIGS. 1A-C, where for the purpose of demonstrating association of the aptamer with a nucleotide sequence, the fluorophore and quencher components may be ignored.

FIG. 1D depicts a general scheme for association of an amine-functionalized aptamer to a surface region of a C-dot. As may be noted, the C-dot is originally provided with surface-exposed carboxyl and amine groups that may be further modified, extended or capped, to permit, inter alia, further chemical association, design and control of substitution density, design and control of population of aptamers that may be associated and others.

The nanoparticles may have any shape, such as round, spherical, cube, cylindrical, fiber, whisker-like or any irregular shape, as known in the art.

In some embodiments, the nanoparticles are of a material permitting stable association with the aptamer and bond dissociation once the aptamer becomes associated with a target.

The nanoparticle material may be selected from carbon-based materials and polymeric materials.

In some embodiments, the nanoparticle material is selected from carbon quantum dots (C-dots), graphene oxide nanoparticles, DNA based nanoparticles, carbon nitride nanoparticles, metal organic framework nanoparticles, polymeric nanoparticles, polysaccharide nanoparticles and any combinations thereof.

In some embodiments, the nanoparticle is a carbon quantum dot (C-dot),

In some embodiments, the material used in fabrication of nanoparticles for, e.g., ocular delivery, may be selected from polyalkyleyanoacrylates, such as poly(ethyleyanoacrylate), poly(butylcyanoacrylate), poly(isobutylcyanoacrylate), poly(hexylcyanoacrylate), poly(hexadecyl cyanoacrylate), or copolymers of alkylcyanoakrylates and ethylene glycol; poly(DL-lactide), poly(L-lactide), poly(DL-lactide-co-glycolide), poly(s-caprolactone), and poly(DL lactide-co-F-caprolactone); Eudragit polymers such as Eudragit RL 100, Eudragit RS 100, Eudragit E 100, Eudragit L 100, Eudragit L 100-55, and Eudragit S 100.

Nanoparticles can be also fabricated from polyvinyl acetate phthalate, cellulose acetate phthalate, hydroxypropyl methylcellulose phthalate, or hydroxypropyl methylcellulose acetate succinate.

In other embodiments, the nanoparticle materials may include natural polysaccharides such as chitosan, alginate, or combinations thereof; complexes of alginate and poly(1-lysine); pegylated-chitosan; natural proteins such as albumin; lipids and phospholipids such as liposomes; or silicon.

In other embodiments, the nanoparticles material may be from a material selected from polyethylene glycol, hyaluronic acid, poly(1-lysine), polyvinyl alcohol, polyvinyl pyrollidone, polyethyleneirnine, polyacrylamride, poly(N-isopropylacrylamide).

Where the nanoparticles are not surface associated with functionalities which permit association to the aptamer, the nanoparticles may be further modified to include such functionalities.

In some embodiments, the vehicle is in the form of a nanoparticle of a size (diameter or longest axis) between 1 to 1,000 nm, between 1 to 900 nm, between 1 to 800 nm, between 1 to 700 nm, between 1 to 600 nm, between 1 to 500 nm, between 1 to 400 nm, between 1 to 300 nm, between 1 to 200 nm, between 1 to 100 nm, between 1 to 90 nm, between 1 to 80 nm, between 1 to 70 nm, between 1 to 60 nm, between 1 to 50 nm, between 10 to 1,000 nm, between 20 to 1,000 nm, between 30 to 1,000 nm, between 40 to 1,000 nm, between 50 to 1,000 nm, between 60 to 1,000 nm, between 70 to 1,000 nm, between 80 to 1,000 nm, between 90 to 1,000 nm, between 100 to 1,000 nm, between 150 to 1,000 nm, between 200 to 1,000 nm, between 250 to 1,000 nm, between 300 to 1,000 nm, between 350 to 1,000 nm, between 400 to 1,000 nm, between 450 to 1,000 nm, between 500 to 1,000 nm, between 550 to 1,000 nm, between 600 to 1,000 nm, between 650 to 1,000 nm, between 700 to 1,000 nm, between 750 to 1,000 nm, between 800 to 1,000 nm, between 850 to 1,000 nm or between 900 to 1,000 nm. In some embodiments, the nanoparticles are between 1 to 500 nm in size.

The "aptamer" is a material capable of binding to a target molecule, the aptamer being in a form of a single- or double-stranded DNA or RNA. The aptamer has an activity in terms of biochemical activity, molecular recognition or binding attributes and may be used in accordance with the invention in methods of prevention, treatment and diagnosis. The aptamer has a molecular activity such as hinging to a target molecule at a specific epitope (region). The aptamer may be synthesized and/or identified by in vitro evolution methods, as known in the art. Means for preparing and characterizing aptamers, including by in vitro evolution methods, are well known in the art, e.g., U.S. Pat. No. 7,939,313. The "aptamer sequence" encompasses an oligonucleotide or a peptide sequence that binds specifically to the OAGF target molecule, in any isoform, mutant or variant thereof. In some embodiments, the aptamer sequence is a single-stranded RNA sequence or a single-stranded DNA sequence. The aptamer sequence may have at least one region complementary to a nucleotide region on the vehicle to permit association via hybridization of the aptamer sequence to a linker sequence on the vehicle, e.g., nanoparticle.

In some embodiments, the aptamer has a sequence selected from:

```
                                      (SEQ ID NO: 3)
    5'-ACCTGGGGGAGTATTGCGGAGGAAGGTT-3',
    and (SEQ ID NO: 4)
    5'-TGTGGGGGTGGACGGGCCGGGTAGA-3'.
```

In some embodiments, the aptamer sequence is 5'-TGTGGGGGTGGACGGGCCGGGTAGA-3' (SEQ ID NO: 4).

In some embodiments, the sequence is a mutated sequence of SEQ ID NO: 3 or SEQ ID NO: 4. The "mutation" may be a single nucleotide variation in the nucleic acid sequences or two or more such variations in two or more positions along the sequences. In some embodiments, a mutation refers to at least a single nucleotide variation in a nucleic acid sequence. In some embodiments, a mutation may include a substitution, a deletion, an inversion or an insertion. In some embodiments, a substitution, deletion, insertion, or inversion may include variation of more than one nucleotide. In some embodiments, a substitution, deletion, insertion or inversion may include variations (substitution, deletion, insertion or inversion) of 1, 2, 3, 4, 5, 6, 7, 8, 9, 10, 11, 12, 13, 14, 15, 16, 17, 18, 19, 20, 21, 22, 23, 24 or more nucleotides.

The "nucleic acid" or "nucleic acid sequence" refers to an oligonucleotide, nucleotide or polynucleotide, and fragments or portions thereof, which may be single or double stranded, as specifically indicated. The nucleic acid may include DNA (or RNA), and may be of natural or synthetic origin.

The "ocular angiogenesis growth factor, OAGF" is a protein associated with at least one of retinal angiogenesis, choroidal angiogenesis, iris angiogenesis and corneal angiogenesis and any combinations thereof. Typically, such a protein binds to cell-surface receptors on the same (autocrine), on a nearby (paracrine) or on a distant (endocrine) cell, typically possessing intrinsic tyrosine kinase activity that couples receptor binding with an intracellular signal that in turn leads to an altered gene transcription, and consequentially to stimulating cell proliferation.

In some embodiments, said OAGF is selected from vascular endothelial growth factor (VEGF), placental growth factor (PLGF), erythropoietin, insulin-like growth factor-1 (IGF-1), hepatocyte growth factor (HGF), angiopoietin (Ang-1 and Ang-2), platelet-derived growth factor (PDGF) and any combinations thereof.

In accordance with the invention, the aptamer is designed or selected to bind or associate with OAGF. The association between the two may be of any form. For example, a single aptamer molecule may bind to each OAGF homodimer, or exhibit a 2:1 stoichiometry (aptamer:OAGF homodimer). Other ratios are also possible.

To ensure delivery of the aptamer to its target, the aptamer is associated or "conjugated" to a vehicle entity, that is, in some embodiments, a nanoparticle. The density of the aptamer on the surface of the vehicle, e.g., nanoparticle, may vary based, inter alia, on the length of the aptamer, the type of conjugation and other characteristics relating, among others, to a population of aptamer/vehicle conjugates. In some embodiments, the density of conjugation on the surface of the vehicle, nanoparticles (e.g., C-dots) is between 0.4 and 1 microMolar per mg of the vehicle (C-dots). In some embodiments, the density is between 0.4 and 0.8 microMolar per mg of the vehicle (C-dots), between 0.4 and 0.6 microMolar per mg of the vehicle (C-dots), between 0.5 and 1 microMolar per mg of the vehicle (C-dots), between 0.5 and 0.9 microMolar per mg of the vehicle (C-dots), between 0.5 and 0.8 microMolar per mg of the vehicle (C-dots), between 0.5 and 0.7 microMolar per mg of the vehicle (C-dots), between 0.6 and 1 microMolar per mg of the vehicle (C-dots), between 0.6 and 0.9 microMolar per mg of the vehicle (C-dots), between 0.6 and 0.8 microMolar per mg of the vehicle (C-dots), between 0.6 and 0.7 microMolar per mg of the vehicle (C-dots), or 0.4, 0.5, 0.6, 0.7, 0.8, 0.9 or 1 microMolar per mg of the vehicle (C-dots).

Unlike association between the aptamer and its OAGF target, association between the aptamer and the vehicle are weaker in comparison. Thus, when the aptamer binds to the target, the weaker association with the vehicle becomes dissociates, partially in view of a possible change in the conformation of the aptamer within the target. The aptamer and vehicle are associated or conjugated to each other through a bond or a linkage or an interaction that holds the two together until such a point when the aptamer becomes associated or bonded to the OAGF. Upon such association with the OAGF, the linkage between the aptamer and the vehicle spontaneously breaks down or dissociates or becomes cleaved. Notwithstanding, the association (direct or indirect, as disclosed herein) that holds the aptamer and the vehicle together, the association needs to be reversible, labile or otherwise reactive to an association between the aptamer and the OAGF. To permit such reversibility, the association between the aptamer and the vehicle is selected from a valance bond, an electrostatic interaction, a hydrogen bond, a metal-metal bond, a sigma bond, a pi-pi bond, a coordination bond or any other reversible association.

The vehicle and the aptamer may be associated via at least one functional group on the vehicle and at least one other functional group on the aptamer. The association of the two is achievable by any means available to the practitioner and may vary depending, inter alia, on the type of vehicle, the vehicle material, the number of aptamer units to be associated with each vehicle, the type of association required, and other parameters.

Thus, an antiangiogenic agent of the invention comprises a vehicle associated, as defined, with an OAGF aptamer; the association between the vehicle and the aptamer is maintained intact such that the vehicle aids in the delivery of the aptamer, increases the stability of the aptamer, or minimize potential interaction with the aptamer and a non-OAGF target. Also, the vehicle aids penetration of the aptamer through the ocular structures, e.g., penetration of the cornea.

Without being bound by theory, it is noted that upon binding of the aptamer to the target OAGF, the conformation of the aptamer may change in a manner that allows or renders facile or drives or causes or catalyzes or activates the dissociation of the aptamer from the vehicle.

In some embodiments, the dissociation is spontaneous and requires no assistance with any auxiliary material. In other embodiments, the dissociation is aided by the use of a biocatalyst that can activate or catalyze the dissociation process.

In cases where the association or conjugation of the aptamer to the vehicle is via a chemical bond, the chemical bond cleaves in such a way that the aptamer is no longer associated with the vehicle or with any chemical group thereof.

In some embodiments, each vehicle is provided with multiple aptamer molecules, differing in the way(s) the aptamers are associated with the vehicle. For example, to permit prolonged delivery of the aptamers, the association of the aptamers with the vehicle may be via different bonds or interaction, whereby each interaction provides a different dissociation or release profile. In some embodiments, the release or dissociation profile provides aptamers in predetermined quantas. In other cases, the release or dissociation profile provide release of the complete amount of the aptamers. In other cases, the release or dissociation profile provides aptamer release continuously over a period of time.

Thus, the invention further provides an antiangiogenic agent comprising a vehicle, e.g., a nanoparticles such as a C-dot, having a plurality of nucleic acids associated therewith, each nucleic acid in said plurality of nucleic acids having a sequence comprising at least 9 nucleic acid bases hybridized to at least 9 nucleic acid bases of a complementary nucleic acid sequence comprised within a sequence of at least one ocular angiogenesis growth factor (OAGF)

aptamer, wherein said hybridization dissociates upon binding of at least one ocular angiogenesis growth factor to said at least one aptamer.

In some embodiments, the agent is adapted for use in a method of inhibiting endothelial cell proliferation, migration, tube formation, or any combination thereof.

In some embodiments, the vehicle in the form of a C-dot is surface-associated with a plurality of nucleic acids, each nucleic acid in said plurality of nucleic acids having a sequence comprising at least 9 nucleic acid bases hybridized to at least 9 nucleic acid bases of a complementary nucleic acid sequence comprised within a sequence of at least one ocular angiogenesis growth factor (OAGF) aptamer.

In some embodiments, the C-dot is surface-associated with each of the nucleic acids via a covalent bond, or a non-covalent interaction.

In some embodiments, the C-dot is functionalized with amine or carboxylic groups which associate to the plurality of nucleic acids.

In some embodiments, the at least a portion of the plurality of nucleic acids associated with the vehicle are single-stranded DNA sequences.

In some embodiments, the at least a portion of the plurality of nucleic acids associated with the vehicle are single-stranded DNA having a sequence consisting or comprising 5'-TCTACCCGGCCC-3' (SEQ ID NO: 1).

In some embodiments, the association between the at least portion of the plurality of nucleic acids and the vehicle is via an extension group comprising between 1 and 10 atoms.

In some embodiments, the extension groups have an end group selected from amine groups, alcohol groups and carboxyl groups.

In some embodiments, the single-stranded DNA sequence is functionalized with an amine extension group.

In some embodiments, the single-stranded DNA has the structure 5'-NH$_2$—(CH$_2$)$_n$-TCTACCCGGCCC-3' (SEQ ID NO:2), wherein n is an integer between 1 and 10.

In some embodiments, the C-dot is surface-associated with a plurality of single-stranded DNA sequences of SEQ ID NO:2, wherein n is 2 or 6.

In some embodiments, the vehicle is a C-dot associated with a plurality of sequences having SEQ ID NO:2, wherein n is 6, each of the plurality of sequences being hybridized to the aptamer. The aptamer is of a sequence selected from:

```
                                    (SEQ ID NO: 3)
    5'-ACCTGGGGGAGTATTGCGGAGGAAGGTT-3',
    and (SEQ ID NO: 4)
    5'-TGTGGGGGTGGACGGGCCGGGTAGA-3'.
```

In some embodiments, the agent of the invention is adapted for use in a method of prevention or treatment of at least one ophthalmic disease or disorder associated with ocular angiogenesis in a subject.

In some embodiments, the agent may be further associated with at least one quencher moiety and optionally at least one fluorophore moiety. Where the vehicle is a fluorophore, e.g., C-dot, the agent may be further associated with at least one quencher moiety and/or at least one another fluorophore.

In embodiments providing composition of the invention a plurality of antiangiogenic agents is provided composed of different populations of such agent, each population being different from another population in one or more of type and form of the vehicle, material composition of the vehicle, the nature of association/bonding between a vehicle and the aptamer, the density of aptamers on each vehicle or vehicle type, the relative amount of one population versus the other and others.

Depending on the nature and compositions of formulations or composition comprising such populations or in general comprising at least one antiangiogenic agent, the compositions or formulations of the invention may comprise one or more biocatalyst. The "biocatalyst" is any type of compound that catalyzes a dissociation of conjugation between the vehicle, e.g., nanoparticle, and the aptamer. The biocatalyst may be endogenous or exogenous and is designed in accordance with the bond to be dissociated, the size and constitution of the aptamer sequence, the rate at which dissociation is desired (so as to control dissociation and a chive a short term or long term dissociation and as a consequence fast or slow association between the aptamer and the OAGF), and so forth. The biocatalyst may be an enzyme or a complex of enzymes, a combination of an enzyme and a co-factor, a biocatalytic RNA molecule, and others.

The biocatalyst may be administered subsequent to the administration of the antiangiogenic agent.

In a further aspect the invention provides a composition comprising at least one antiangiogenic agent according to the invention.

In some embodiments, the composition comprises at least one biocatalyst.

In some embodiments, the composition may further comprise one or more inactive ingredients such as concentration and tonicity adjusting agents, a buffer and pH adjusting agents, stabilizers, preservatives and agents for preventing material decomposition, solubility modifiers, viscosity modifiers, antioxidants, surface active agents, polysaccharides, and others.

In some embodiments, a composition of the invention further comprises at least one additional active agent, that is optionally selected from another antiangiogenic agent, a drug for the prevention or treatment of an eye disease or disorder, and any drug or active known for ophthalmic use.

In some embodiments, a composition of the invention is a topical composition namely a composition that does not result in a systemic effect. In other embodiments, the composition is an intraocular composition. In some embodiments, the composition is in the form suitable for the application to the eye, e.g., a cream, an emulsion, a dispersion, a foam, an oily solution, an aqueous solution, a lotion, aqueous or oily eye drops, eye ointment, paper strips, ocuserts, hydrogel contact lenses, collagen shields, ophthalmic rods and any other form known in the art. The present invention thus also relates to compositions, which are pharmaceutical compositions, or ophthalmic compositions, comprising at least one antiangiogenic agent in admixture with pharmaceutically acceptable auxiliaries, and optionally other therapeutic agents. The auxiliaries must be pharmaceutically acceptable in the sense of compatible with other ingredients of the composition and not deleterious to the recipients thereof.

Additionally, to maintain ocular retention of the agents of the invention once administered to the eye topically, e.g., by eye drops, internalization of the agent into the corneal and/or conjunctival cells of the ocular epithelium may be achieved by suitable selection of non-active carriers. Such carriers may be selected amongst biocompatible, non-irritant polymeric permeability enhancers. Non-limiting examples include chitosan, xyloglucan, arabinogalactan, cellulose derivatives (e.g., methylcellulose, hydroxyethyl cellulose, hydroxypropylmethylcellulose, sodium carboxymethylcellulose), hyaluronic acid, alginic acid and gellan gum.

Pharmaceutical compositions include those suitable for topical application, including transdermal, ophthalmological administration or intraocular injection or administration via an implant. The compositions may be prepared by any method known in the art.

In yet another aspect the invention provides an antiangiogenic agent or a composition comprising same, as disclosed herein, for use in the prevention or treatment of at least one ophthalmic disease or disorder associated with ocular angiogenesis in a subject in need thereof.

The invention further provides antiangiogenic agent or a composition comprising same, as disclosed herein, for use in a method of preventing or treating at least one ophthalmic disease or disorder associated with ocular angiogenesis in a subject in need thereof.

In some embodiments, the disease or disorder associated with ocular angiogenesis may be any condition in a patient that is associated with ocular angiogenesis (e.g., retinal angiogenesis, choroidal (subretinal) angiogenesis, and corneal angiogenesis and any combinations thereof). Retinal angiogenesis, typically seen in proliferative diabetic retinopathy, retinal vein occlusion or retinopathy of prematurity, is the consequence of an abnormal vascular response to retinal ischaemia or hypoxia. During retinal angiogenesis retinal vascular endothelial cells start to proliferate through the internal limiting membrane into the vitreous, where they may cause vitreous haemorrhage or tractional retinal detachment. In the neovascular form of AMD choroidal vessels grow through the degenerated Bruch's membrane into the subretinal space, causing subretinal exudation and haemorrhage. Neovascularization of the cornea compromises its transparency and leads to severe visual impairment. It is a common clinical problem seen in response to chronic hypoxia or various inflammatory stimuli, such as infectious keratitis, alkali burns and graft rejections. Corneal angiogenesis emerges from the limbal vessels and therefore ocular surface disorders predispose to superficial neovascularization, while stromal keratitis causes deep infiltration of vessels.

The ophthalmic disease or disorder is any disease or disorder of the eye or related tissues. Non-limiting examples include macular degeneration, age related macular degeneration, wet macular degeneration, dry macular degeneration, diabetic retinopathy, retinopathy of prematurity, neovascular glaucoma, rubeosis, corneal neovascularization, corneal graft rejection, retrolental fibroplasia and any combination thereof.

In some embodiments, the disease or disorder is selected from macular degeneration, age related macular degeneration, wet macular degeneration, dry macular degeneration, diabetic retinopathy and any combinations thereof.

Compositions of the invention may be administered topically to an eye of a subject. In some embodiments, the subject is further treated with an antiangiogenic agent that is different from an agent of the invention and which may be administered concurrently, in a different or the same composition, or sequentially, or at different time points to the agent of the invention.

In a further aspect the invention provides a method of preventing or treating an ophthalmic disease or disorder associated with ocular angiogenesis in a subject, the method comprising administering to said subject an antiangiogenic agent or a composition of the invention.

The term "prevention or treatment" or any lingual variation thereof refers to the administering of a therapeutic amount (effective amount) of an agent of a composition of the invention which is effective to ameliorate undesired symptoms associated with a disease, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to bring about rapid recovery, or to prevent the disease form occurring or a combination of two or more of the above.

The exact dose and regimen of administration of a composition according to the invention will necessarily be dependent upon the therapeutic effect to be achieved and may vary with the particular formula, the route of administration, and the age and condition of the individual subject to whom the composition is to be administered. In general terms, the amount of the aptamer that is effective in prophylaxis or treatment according to the invention, referred to as the "effective amount", may be determined by such considerations as may be known in the art. The amount must be effective to achieve a desired therapeutic effect as described above, depending, inter alia, on the type and severity of the disease to be treated and the treatment regime. The effective amount may be determined in appropriately designed clinical trials (dose range studies) and the person versed in the art will know how to properly conduct such trials in order to determine the effective amount.

The antiangiogenic agent of the invention may be substituted with a fluorophore component and a quencher component to thereby provide a diagnostic tool for diagnosing or monitoring state of a disease or a disorder, or predict susceptibility for suffering from a disease or disorder as herein defined. The diagnostic tool thus obtained is regraded herein as a conjugate comprising: (a) a vehicle in the form of at least one fluorophore component; or a vehicle associated to at least one fluorophore component; (b) at least one quencher component; and (c) at least one ocular angiogenesis growth factor aptamer ("aptamer", as used herein). In the conjugate, the at least one aptamer is associated with the at least one or both of fluorophore component and the at least one quencher component; and wherein upon binding of the aptamer to OAGF, said fluorophore component and/or quencher component become dislocated or detached.

The invention further provides a conjugate comprising: (a) a nanoparticle having a plurality of nucleic acids associated therewith, each nucleic acid in said plurality of nucleic acids having a sequence comprising at least 9 nucleic acid bases hybridized to at least 9 nucleic acid bases of a complementary nucleic acid sequence comprised within a sequence of at least one ocular angiogenesis growth factor (OAGF) aptamer; (b) at least one fluorophore moiety, where the nanoparticle is not a fluorophore; and (c) at least one quencher moiety; wherein said at least one aptamer is associated with the at least one or both of fluorophore moiety and the at least one quencher moiety; and wherein upon binding of the aptamer to at least one ocular angiogenesis growth factor, said fluorophore moiety and/or quencher moiety are dissociated. The conjugate is optionally for use in a method of determining an amount of at least one ocular angiogenesis growth factor in a subject eye.

In some embodiments, the conjugate is provided wherein the nanoparticle a fluorophore, e.g., a C-dot.

The invention further provides a conjugate which comprises: (a) a C-dot having a plurality of nucleic acids associated with its surface, each nucleic acid in said plurality of nucleic acids having a sequence comprising at least 9 nucleic acid bases (b) at least one ocular angiogenesis growth factor (OAGF) aptamer hybridized to the nucleic acids on the surface of the C-dot, wherein said hybridization being via at least 9 nucleic acid bases of a complementary nucleic acid sequence comprised within a sequence of at least one aptamer; and (c) at least one quencher moiety; wherein said at least one aptamer is associated with the at least one quencher moiety.

The fluorophore component and the quencher component may be positioned in the conjugate in a variety of forms relative to the aptamer. As shown in FIG. 1A, the fluorophore (F) is associated with at least one nucleotide sequence and the quencher (Q) is associated with at least one other nucleotide sequence, the at least one nucleotide sequence associated to the fluorophore and the at least one other nucleotide sequence associated to the quencher comprise a sequence region complementary to the aptamer sequence, such that upon association of the aptamer with the OAGF, both sequences become dissociated and fluorescence is emitted; the fluorescence may be detected and quantified to determine whether the aptamer has been associated with the OAGF and the relative amount of associations (as determined based on a preset ladder).

A second embodiment is depicted in FIG. 1A, wherein the aptamer is associated at one terminus with a fluorophore component and at its other terminus with a quencher component. In the folded state, due to proximity in space, the quencher component quenches fluorescence. Once the aptamer becomes associated to the OAGF, the two components become distant in space, thereby reducing the quenching effect (fluorescence occurs and measured/quantified).

A similar association is presented in FIG. 1B, wherein the fluorophore component is a nanoparticle, e.g., C-dot, which upon association of the aptamer with the OAGF, the nucleotide sequence associated with the quencher component becomes dissociated from the aptamer, thereby causing fluorescence to occur.

Where the aptamer is surface associated with a nanoparticle or a vehicle, as shown in general in FIG. 1C, wherein the nanoparticle or vehicle is a fluorophore, e.g., C-dot, the quencher component may be associated to either end of the aptamer. When association occurs, fluorescence is quenched. However, upon association with the OAGF, the nanoparticle or vehicle becomes detached from the aptamer, and fluorescence is regenerated.

The "fluorophore component" used in conjugates of the invention is a compound or a part of a compound (e.g., a functional group) that emits light upon light excitation (fluoresces). The fluorophore may be associated with the aptamer via any labile bond or association. The labile bond or association that holds the aptamer and the fluorophore component together needs to be reversible, labile or reactive to an association between the aptamer and the OAGF. To permit such reversibility, the association between the aptamer and the fluorophore component is selected from a valance bond, an electrostatic interaction, a hydrogen bond, a metal-metal bond, a sigma bond, a pi-pi bond, a coordination bond or any other reversible association.

In some embodiments, the at least one fluorophore component is selected from carbon quantum dots (C-dots), graphene oxides, metallic quantum dots, organic protein fluorophores of organic non-protein fluorophores or any combinations thereof.

In some embodiments, the at least one fluorophore component is selected from silica and modified silica, hydrophobic and hydrophilic organic polymers, semiconducting organic polymers, carbonaceous nanomaterials such as carbon quantum dots, carbon nanoclusters, carbon nanotubes, nanodiamonds, upconversion materials, metal particles and metal oxides.

In some embodiments, the at least one fluorophore component is selected from fluorescent nanodots of semiconducting polymer blends which may optionally be attached or associated with peptides such as chlorotoxin.

In other embodiments, the at least one fluorophore component is selected from tetraphenylethene-based fluorescent organic nanoparticles.

In other embodiments, the at least one fluorophore component is selected from carbon dots (C-dots). The C-dots may be in the form of clusters of carbon atoms with diameters of typically 2 to 8 nm.

In other embodiments, the at least one fluorophore component is selected from graphite oxide and graphene.

In some embodiments, the at least one fluorophore is selected from Fluorescin, Cyanine3, Cyanine5, Tamra, Texas Red and Rhodamine.

Other fluorophores are also available, as disclosed for example in "An overview of nanoparticles commonly used in fluorescent bioimaging", Otto S. Wolfbeis, Chem. Soc. Rev., 2015, 44, 4743-4768.

The "quencher component" is any compound or a part of a compound (e.g., a functional group) that is capable of reducing or eliminating emission from the fluorophore component when attached thereto. Quenching may result from transient excited-state interactions (collisional quenching) or from formation of nonfluorescent ground-state species. Self-quenching may also be used, involving quenching of one fluorophore by another. For example, in fluorescence resonance energy transfer (FRET) a strongly distance-dependent excited-state interaction occurs in which emission of one fluorophore may be coupled to the excitation of another. Because the effect depends on the interaction of adjacent fluorophores, self-quenching, FRET and excimer formation can be exploited for monitoring a wide array of molecular assembly or fragmentation or dissociation processes such as those disclosed herein.

However, quenching may occur by any of several mechanisms including, not only by fluorescence resonance energy transfer (FRET). Other quenching mechanisms may include photoinduced electron transfer, paramagnetic enhancement of intersystem crossing, Dexter exchange coupling and exciton coupling such as the formation of dark complexes. The identity of the quencher moiety may be selected based on any one of a variety of parameters known to a person of skill in the art.

In some embodiments, the at least one quencher component is selected from black hole quenchers, electron transfer quencher, fluorescence resonance transfer quenchers or any combinations thereof.

In some embodiments, the at least one quencher component is selected from Iowa Black FQ and Black Hole Quencher (BHQ-3).

As stated above, the at least one aptamer may be associated with at least one of (a) at least one fluorophore component and (b) at least one quencher component. In some embodiments, the aptamer is associated with at least one fluorophore component. In other embodiments, the aptamer is associated with at least one quencher component. In some embodiments, the aptamer is associated with at least one fluorophore component and with at least one quencher component.

The association of the aptamer with at least one of (a) at least one fluorophore component and (b) at least one quencher component may be a direct association, wherein the at least one aptamer is directly bonded or coordinated with said at least one component. In some other embodiments, said association is an indirect association, wherein the at least one aptamer is bonded or coordinated with a further linking element, for example a sequence that may be coordinated with at least a part of the aptamer sequence, that is directly bonded to said at least one component.

Upon binding of at least one OAGF to the aptamer, said fluorophore component and quencher component are dislocated, dislodged or disconnected, i.e. they become displaced spatially from each other, in a manner that allows the fluorophore to emit light or increase emission of light upon light excitation. In some embodiments, said dislocation relates to dissociation between the components or to spatial displacement of the components, such that the distance between the two components is increased without dissociation occurring between the components.

The fluorescence emission may be detected and quantified as known in the art. For example, fluorescence instruments that may be used include:

Spectrofluorometers and microplate readers that measure the average properties of bulk samples.

Fluorescence microscopes that resolve fluorescence as a function of spatial coordinates in two or three dimensions for microscopic objects.

Fluorescence scanners, including microarray readers, that resolve fluorescence as a function of spatial coordinates in two dimensions for macroscopic objects.

Flow cytometers that measure fluorescence per cell in a flowing stream, allowing subpopulations within a large sample to be identified and quantitated.

Other types of instrumentation that may be used.

The invention further provides a composition comprising at least one conjugate as defined herein. In some embodiments, said composition is as defined herein in reference to any agent or component of the invention.

In another one of its aspects the invention provides a composition comprising at least one conjugate as disclosed herein above, for use in a method of measuring levels of at least one OAGF in an eye of a subject. In some embodiments, the measurement of levels of at least one OAGF in the eye allows for the customization of an antiangiogenic treatment of said subject, wherein optionally the treatment is in accordance with methods of the invention.

In another one of its aspects the invention provides a composition comprising a conjugate as disclosed herein, for use in diagnosis of at least one ophthalmic disease or disorder associated with said at least one OAGF in a subject.

In some embodiments, said ophthalmic disease or disorder is selected as above.

The invention further provides a method of measuring levels of at least one OAGF in an eye of a subject, said method comprising administering to said subject a composition comprising at least one conjugate as disclosed herein.

The invention further provides a method of diagnosing at least one ophthalmic disease or disorder associated with said at least one OAGF in a subject, said method comprising administering to said subject a composition comprising at least one conjugate as disclosed herein.

Each diagnostic method of the invention may comprise one or more additional steps of detecting whether fluorescence has been emitted and quantifying fluorescence emission, to quantify levels of OAGF, to quantify or assess binding of the aptamer to the target, to determine changes in OAGF levels over time to thereby determine susceptibility or evolution of disease states, to permit early detection of a disease or disorder characterized by increased levels of OAGF, and others. The quantification methods may be based on a quantitative ladder predetermined for a particular aptamer or target.

When referring to "diagnosis" it should thus be understood to also encompass a medical diagnosis process for determining which disease or condition a patient is suffering from, that can explain symptoms and signs the patient is exhibiting. In some embodiments, a composition of the invention is administered to a patient thereafter a diagnostic tool is used to detect changes to the composition allowing for the detection of the compounds administered thus diagnosing if the patient suffers from a condition or disease associated therewith.

Within the context of the present invention, the diagnostic tool provided herein permits one or more of the following:

1. Detection or determining early stages of a disease— OAGF can be high before any pathological structural changes or symptoms appear. Early treatment in these cases can be advantageous over treatment in later stages 2. Monitoring success of drug treatment—Current treatment is performed as a routine 1/month or 1/6 weeks protocol(s). Adjusting treatment to OAGF is advantageous to provide better treatment modalities.

3. Deciding which drug is suitable—In some cases, OAGF levels may not be high and other drugs (e.g. steroids) should be considered.

4. Prevention—Very early treatment before any changes appear may be considered therapeutically superior to treatment or elimination of already existing damages.

Thus the invention further provides a method of measuring levels of at least one OAGF in an eye of a subject, said method comprising topically administering to the eye of said subject a composition comprising at least one conjugate and measuring fluorescence emitted following administration, wherein the level of fluorescence being indicative of the level of at least one OAGF in the eye. The nanoparticle is typically a C-dot.

A method is also provided for diagnosing at least one ophthalmic disease or disorder associated with increased level of at least one OAGF in a subject, said method comprising topically administering to the eye of said subject a composition comprising at least one conjugate and measuring fluorescence emitted following administration, wherein the level of fluorescence being indicative of the level of the at least one OAGF in the eye and occurrence of said disease or disorder.

The methods of the invention may be used for determining early stages of a disease, for monitoring success of drug treatment, or for determining suitability of existing treatment. As such, in the methods of diagnosis, the subject is optionally administered with a further amount of the conjugate or an agent according to the invention to affect prevention or treatment of at least one disease or disorder associated with ocular angiogenesis.

The composition used in methods of the invention may therefore comprise an effective amount of the conjugate/ agent that is sufficient to prevent or treat at least one disease or disorder associated with ocular angiogenesis, as defined herein. The administration of the composition may be repeated two or more times to enable diagnosis over time, and optionally further administration of compositions comprising the conjugate and/or an agent to affect prevention or treatment of a disease or disorder associated with ocular angiogenesis.

The invention further provides a sense and treat method comprising (a) a diagnostic method of the invention; and (b) a method of prevention or treatment according to the invention.

The invention further provides a device for measuring qualitatively or quantitatively at least one OAGF levels directly in a subject eye, the device comprising an optical unit comprised of various lenses, light sources and filters capable of detecting florescence emission from at least one fluorophore component of a conjugate administered to said subject; said conjugate comprising: (a) at least one fluorophore component; (b) at least one quencher component; and (c) at least one aptamer; wherein said at least one aptamer is associated with at least one of fluorophore component and quencher component; and wherein upon binding of at least one OAGF to said aptamer, said fluorophore component and/or quencher component are dislocated.

In some embodiments, said device is configured for qualitatively measuring at least one OAGF directly in a subject eye. Thus, the device of the invention is capable of detecting that the subject's eye contains at least one OAGF.

In other embodiments, said device is configured to quantitatively measure at least one OAGF directly in a subject eye. Thus, the device of the invention is capable of detecting the amount of at least one OAGF contained in the eye of said subject.

In some embodiments, in a device of the invention said at least one OAGF is associated with at least one ophthalmic disease or disorder. Thus, using a device of the invention allows diagnosis of at least one ophthalmic disease or disorder, including its stage and progress.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1D provides a general scheme for chemically modifying a C-dot to permit association with an amine-associated aptamer.

DETAILED DESCRIPTION OF EMBODIMENTS

FIGS. 1A-D depict general constructions of antiangiogenic agents and diagnostic tools according to the invention, as further explained herein. The experiments described herein and data provided have been mainly generated on C-dot systems, wherein the aptamer is associated to the C-dot as depicted, for general purposed, in FIG. 1D.

Figure 9:
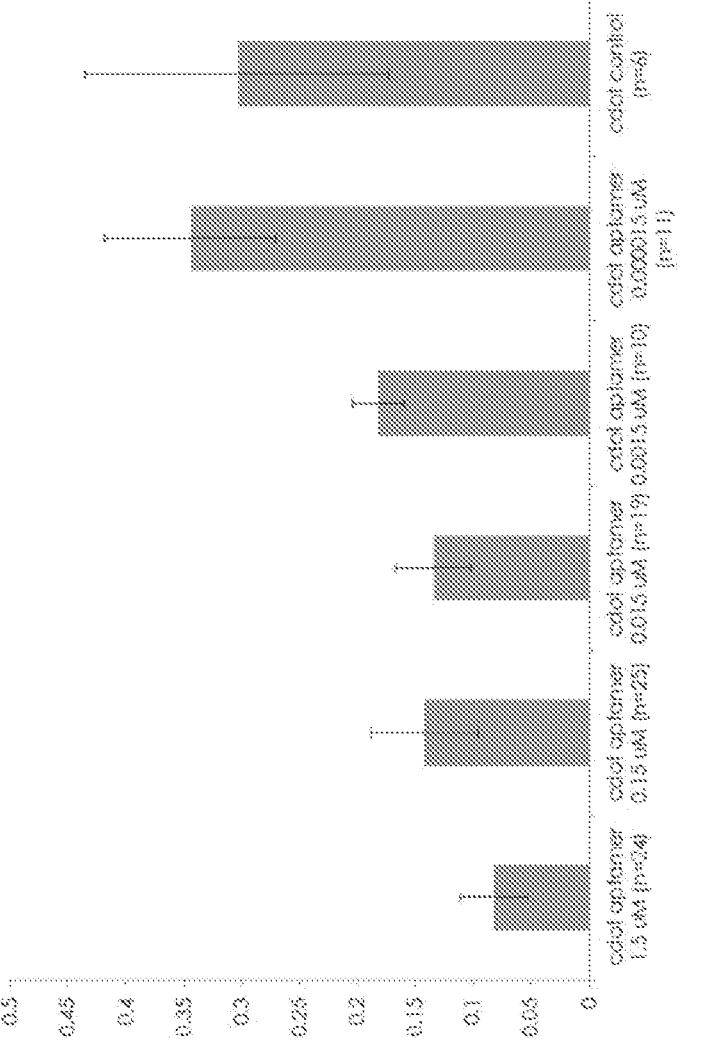
FIG. 9 demonstrates the effect of C-dot aptamer on inhibition of choroidal blood vessels in vitro.

As may be realized from the data provided herein, the effect of C-dot-aptamer complex was shown to significantly inhibit growth of blood vessels in the choroid in an in vitro model of eye explants (FIG. 9). The effect was similar to common anti VEGF agents, which are given by intraocular injections. Thus, results presented herein may be extrapolated to other nanoparticles, aptamers and modes of conjugation.

The inventors of the technology disclosed herein have developed a breakthrough approach in which treatment of certain ophthalmological conditions is achieved by topically administering a drug, thereby eliminating the need for conventional repeated injections. The technology further provides the ability to maintain and monitor treatment efficacy by optical non-invasive measurement of ocular vascular endothelial growth factor (VEGF) levels, and other factors involved in the pathogenesis of blood vessels in the eye, thereby in fact, providing a "sense and treat" methodology. This approach has two main advantages over current available treatment modalities: first, it is capable of measuring the level of VEGF in the vitreous cavity, enabling treatment to be modified accordingly and customized per the patient's needs; and second, it can be applied topically, eliminating the need for repeated intraocular injections.

Carbon nanoparticles (C-dots) (2-3 nm) or graphene oxide (GO) nanoparticles are biocompatible and exhibit high luminescence properties. Single-stranded nucleic acids adsorb onto the graphitic nanomaterials, and upon using quencher-modified single-stranded nucleic acids, quenching of the C-dot or GO nanoparticles proceed.

Figure 1A:
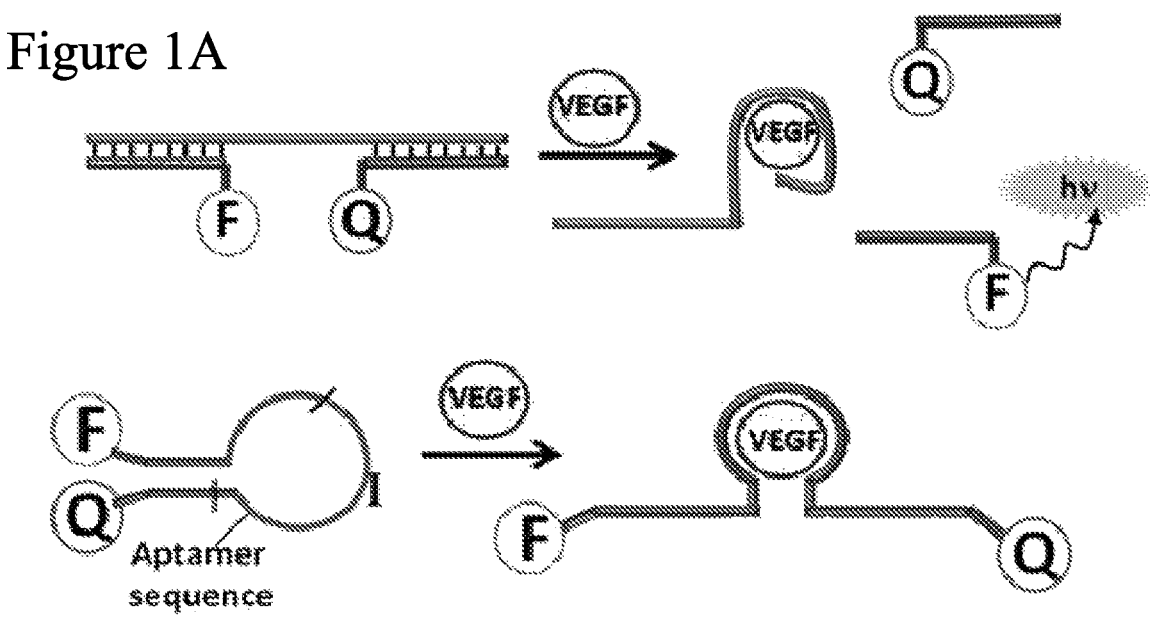
FIGS. 1A-D depict various modes of association between a vehicle, e.g., a nanoparticle, and an aptamer, according to embodiments of the invention. When considered a therapeutic tool, the fluorophore (F) and quencher (Q) components may be ignored, while for the diagnostic aspect of the invention, either or both components are utilized.
Figure 1B:
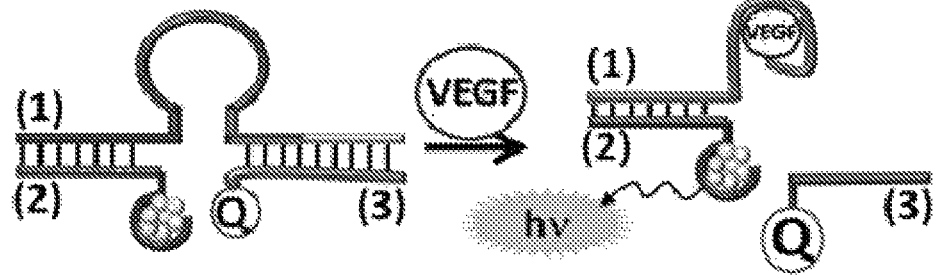
Figure 1C:
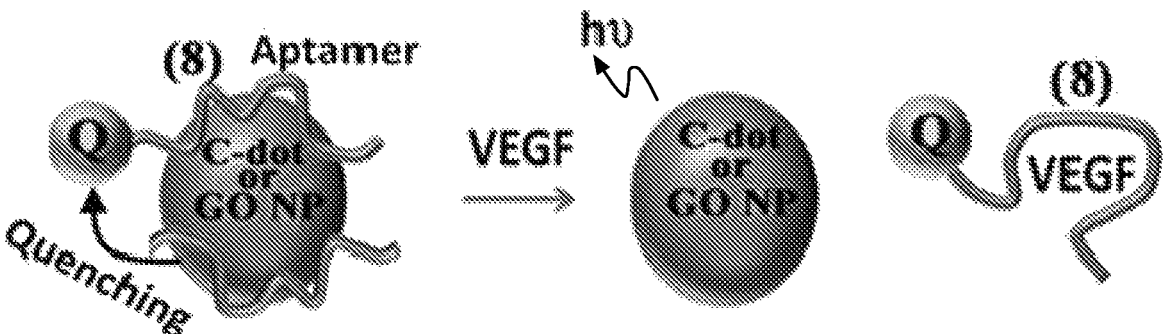
Figure 1D:
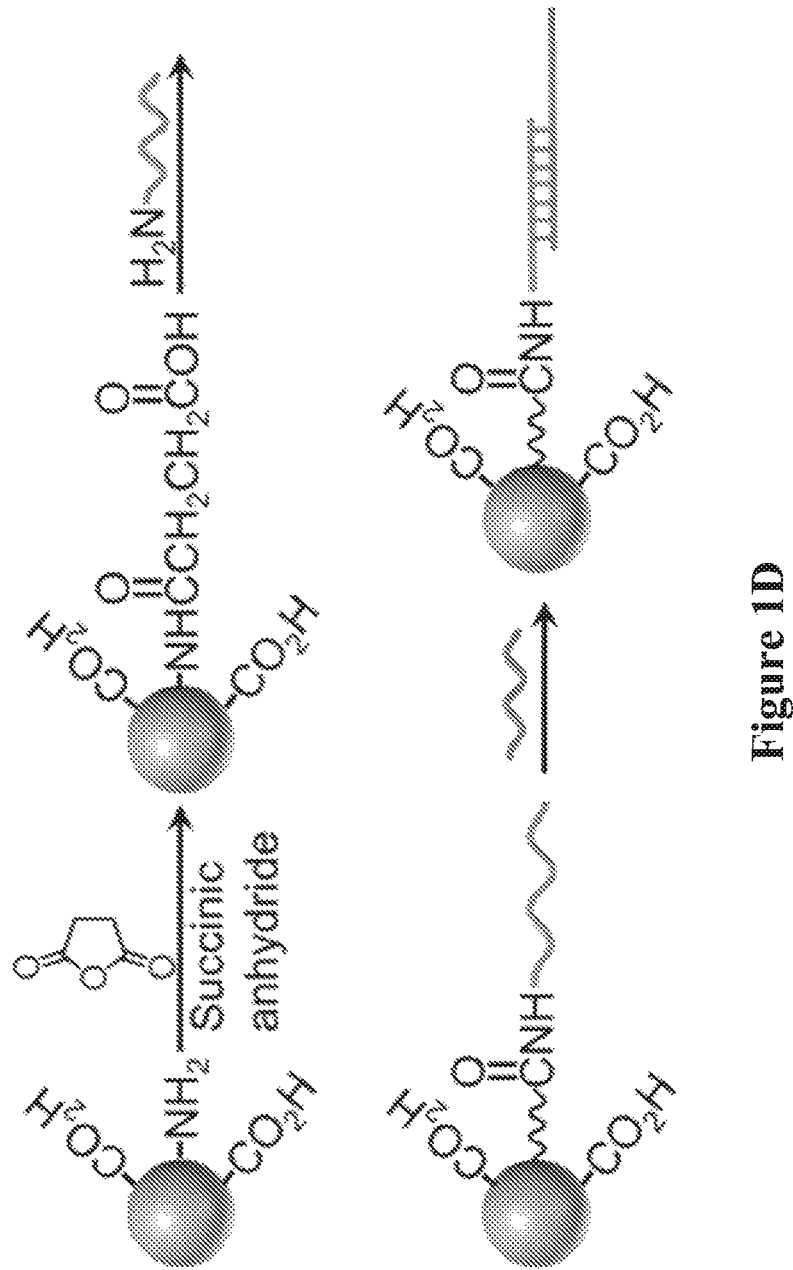

The aptamer-based sensing platforms of VEGF are exemplified in FIGS. 1A-C. In one configuration shown in FIG. 1A, the aptamer sequence is caged by duplexes that include a fluorophor-functionalized nucleic acid and a quencher-modified nucleic acid. The fluorophore is quenched in the supramolecular structure. The formation of the aptamer-VEGF complex releases the fluorophore-labeled nucleic acid, resulting in the triggered-on fluorescence. Alternatively, a hairpin structure is modified at its 5' and 3' ends with a fluorophore quencher pair. The hairpin includes a caged sequence of the anti-VEGF aptamer, and the fluorescence of the fluorophore is quenched in the hairpin configuration. In the presence of VEGF, the formation of the aptamer-VEGF complex opens the hairpin, resulting in the switched-on fluorescence of the fluorophore. In a second sensing platform, shown in FIG. 1B, a supramolecular structure consisting of a nucleic acid (1) that includes the caged sequence of the VEGF aptamer is hybridized with the nucleic acid (2)-stabilized nanocluster, such as C-dot, and with a quencher functionalized nucleic acid, (3), to yield the sensing platform. In the presence of VEGF, the aptamer is uncaged, through the formation of the aptamer-ligand complex, leading to the release of the quencher-modified nucleic acid (3) and to the triggered-on luminescence of the nanocluster. The use of carbon nanomaterials (C-dots or graphene oxide GO nanoparticles) for the development of a luminescent VEGF sensing platform is shown in FIG. 1C. The quencher-functionalized aptamer sequence (8) is adsorbed on the surface of C-dots or GO nanoparticles, leading to the quenching of the luminescence of the nanostructures. The VEGF-stimulated release of the VEGF-aptamer complexes triggers-on the luminescence of the two different carbon-based nanomaterials.

In all sensing platforms, the resulting VEGF-induced luminescence relates directly to the concentration of VEGF. Accordingly, the development of the different sensing platforms includes evaluation of the resulting luminescence intensities as a function of VEGF concentration and the extraction of the respective calibration curves and detection limits for analysis of VEGF. All of the sensing platforms are based on the uncaging of the aptamer sequence or its desorption from the vehicle via the formation of aptamer-VEGF complexes. The time-interval for uncaging the aptamer sequences and the content of the released aptamer-VEGF complex are used to control the sensitivity of the sensing platform. Accordingly, the sensitivity of the sensing platforms, such as those shown in FIG. 1, may be optimized by structural alteration of the nucleic acids involved with the sensing systems.

EXAMPLE 1

In Vivo Model for C-Dot Penetration to the Eye

Methods: C-dots NPs were applied on rat eyes for 1 hour at different concentrations. The aqueous humour (AH), vitreous humour (VH), lens and cornea were collected from each eye and. Fluorescence intensity in the samples was measured by a plate reader and the concentration (mg/ml) of the NP was calculated according to calibration curves tested previously. In another set of experiments the corneal epithelium of the eye was scraped before the NP were instilled. In addition, histological sections were prepared from treated and untreated eyes the florescence of the section was photographed using a florescence microscope.

Figure 2A:
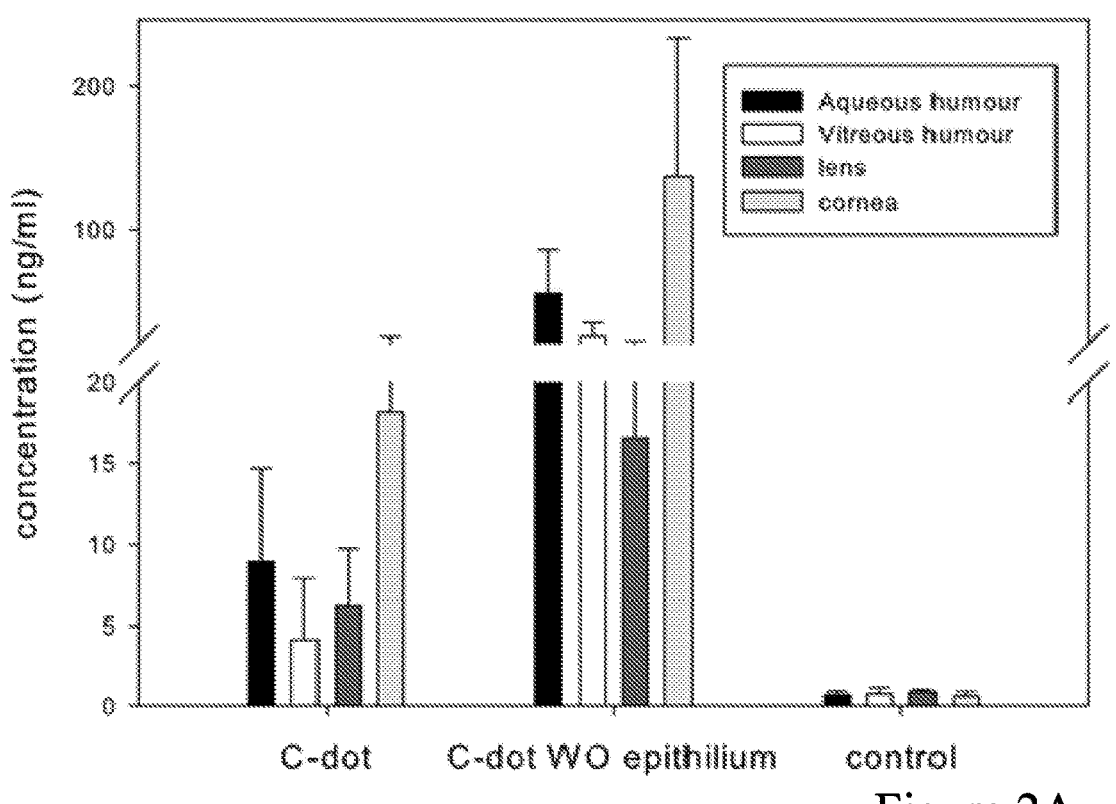
FIGS. 2A-2B show the mean (SD) C-dot concentrations in the aqueous humor (AH), vitreous humor (VH), cornea and lens (FIG. 2A) and histological sections of the C-dot fluorescence in the eye structures including the retina (FIG. 2B).
Figure 2B:
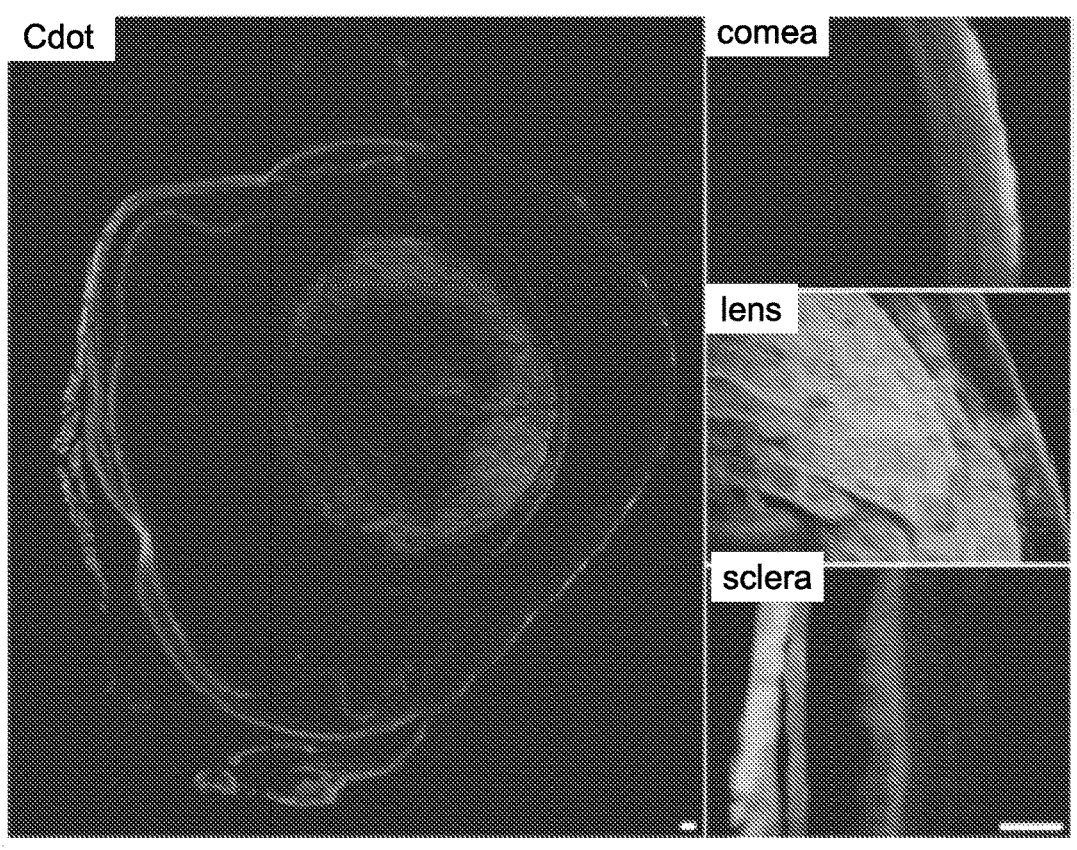

Results: In the C-dot treated eye, the mean (SD) C-dot concentrations in the AH, VH, cornea and lens were 8.9 (5.7), 8.9 (5.7), 6.2 (3.6) and 18.2 (8.0) ng/ml, respectively (FIG. 2A). Mechanical removal of this layer before instilling the NP, resulted in almost a tenfold increase in C-dot ocular concentration, compared to eyes with intact epithelium (FIG. 2, C-dot WO epithelium), indicating the great impact of the corneal epithelium on the NP penetration. Histological sections showed the distribution of the C-dot fluorescence in the eye structures including the retina (FIG. 2B).

EXAMPLE 2

In Vivo Monitoring of C-Dot Florescence in Rat Eyes

Methods: C-dot NPs were instilled on rat's eyes for 1 hour. Using live imaging microscope (micron IV, Phoenix Research Laboratories) we measured the fluorescence of the C-dot in the retina and the VH of live animals up to 24 hours following treatment.

Figure 3A:
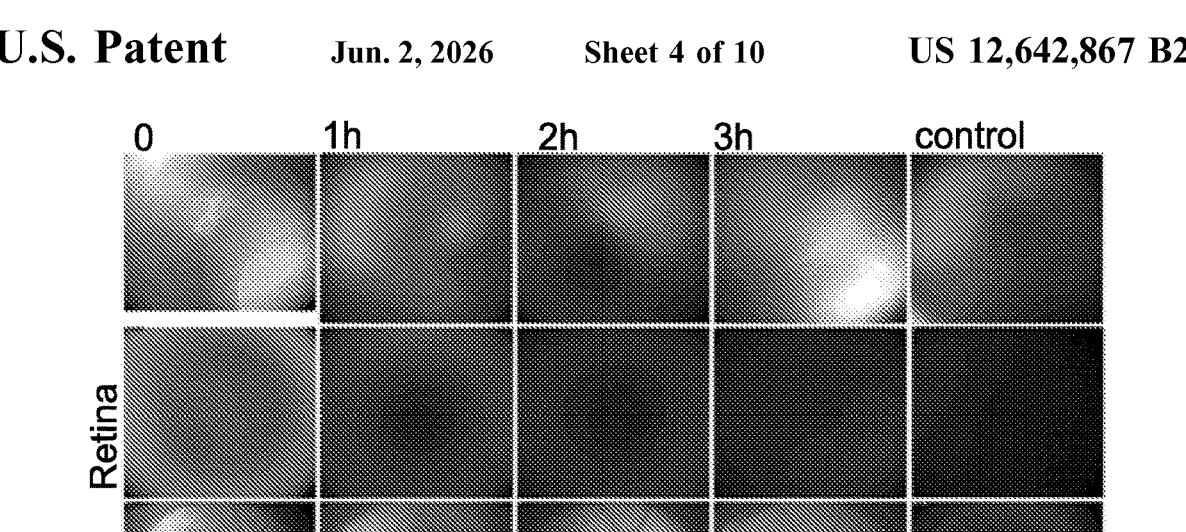
FIGS. 3A-3B show the live imaging microscope (FIG. 3A) of the fluorescence of C-dots in the retina and the VH of live animals up to 24 hours following treatment and fluorescence measurements thereof (FIG. 3B).
Figure 3B:
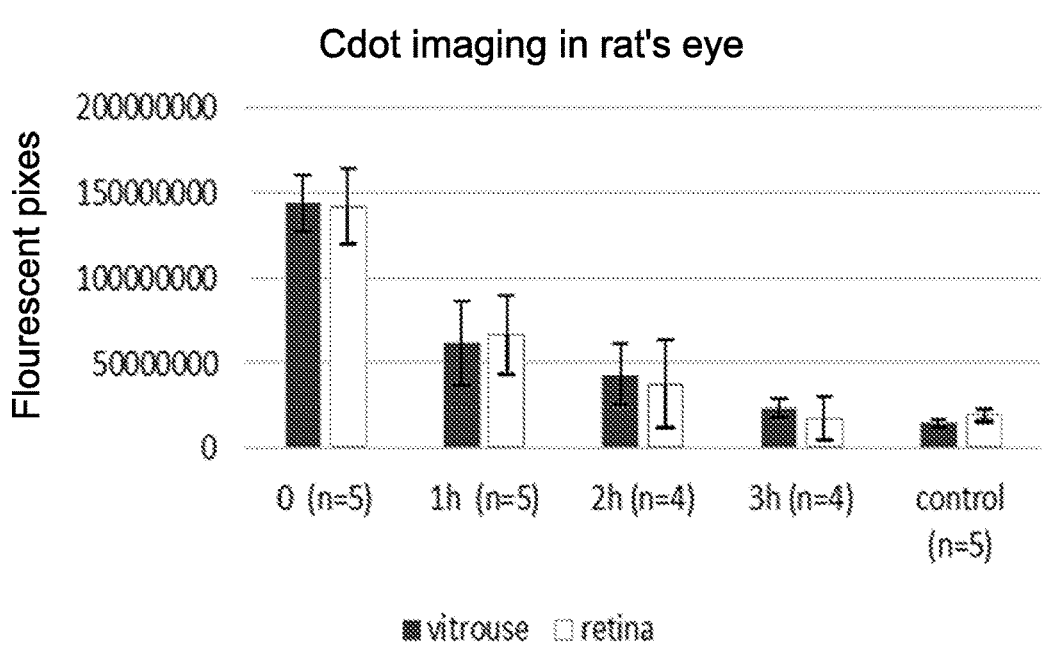

Results: The florescence of the C-dot is detectable in the live animal (images in FIG. 3A). The results show a characteristic clearance during the first three hours after treatment (FIG. 3B).

EXAMPLE 3

In Vitro Toxicity of C-Dot Solution

C-dots are not showing any signs for toxicity to cells in culture.

Methods: In order to evaluate the C-dot solution toxicity to the eye, we used MTT assay on several cell types (fibroblasts, ARPE-19 and MeWo cells). Cells were cultured in the presence of C-dot solution in various concentrations and the viability of the cells was evaluated by measuring the absorbance at $\lambda=570$ nm.

Figure 4:
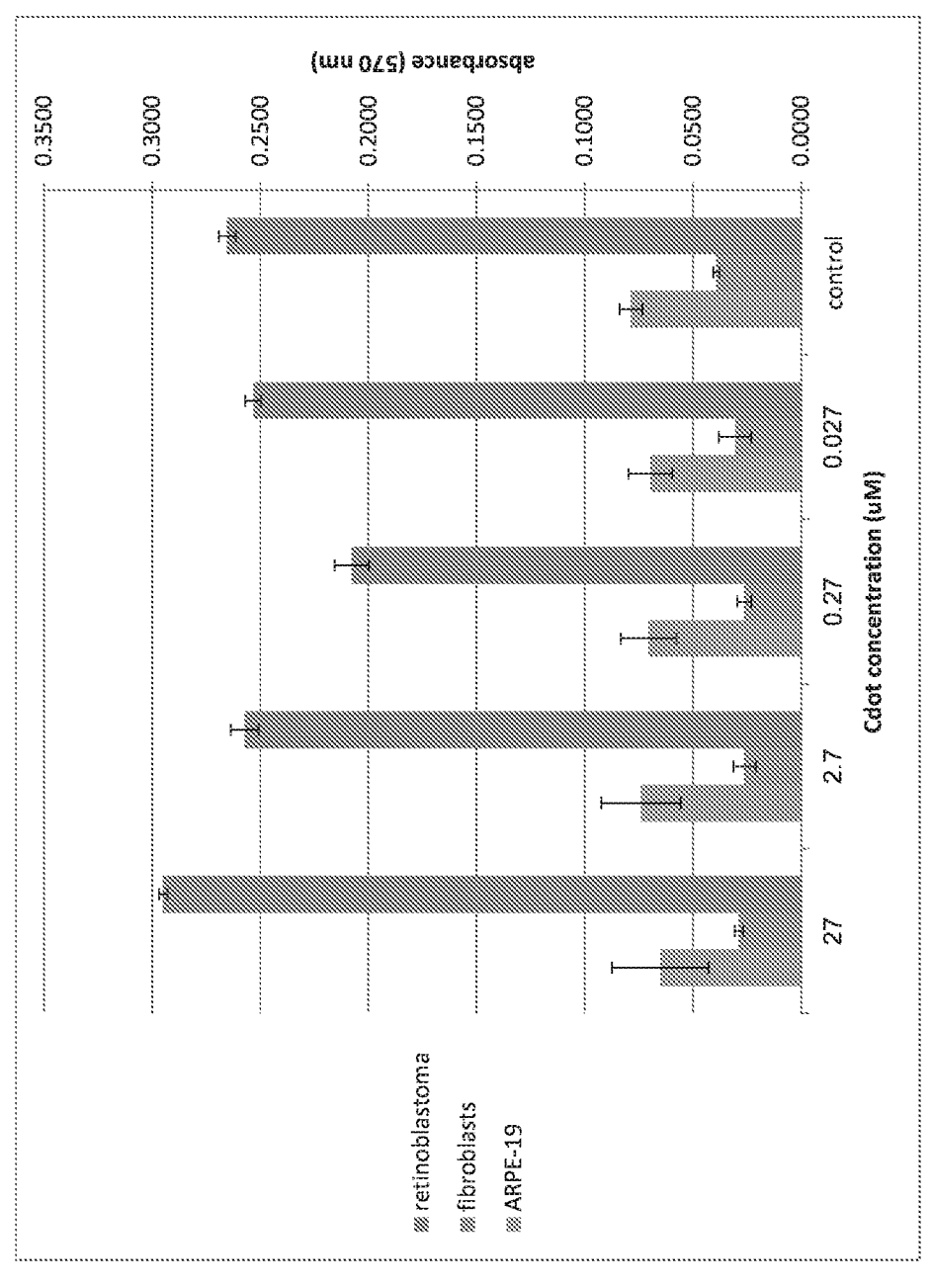
FIG. 4 shows no evidence for C-dot toxicity for three cell types for different concentrations of C-dots, as presented in Example 3.
Figure 5:
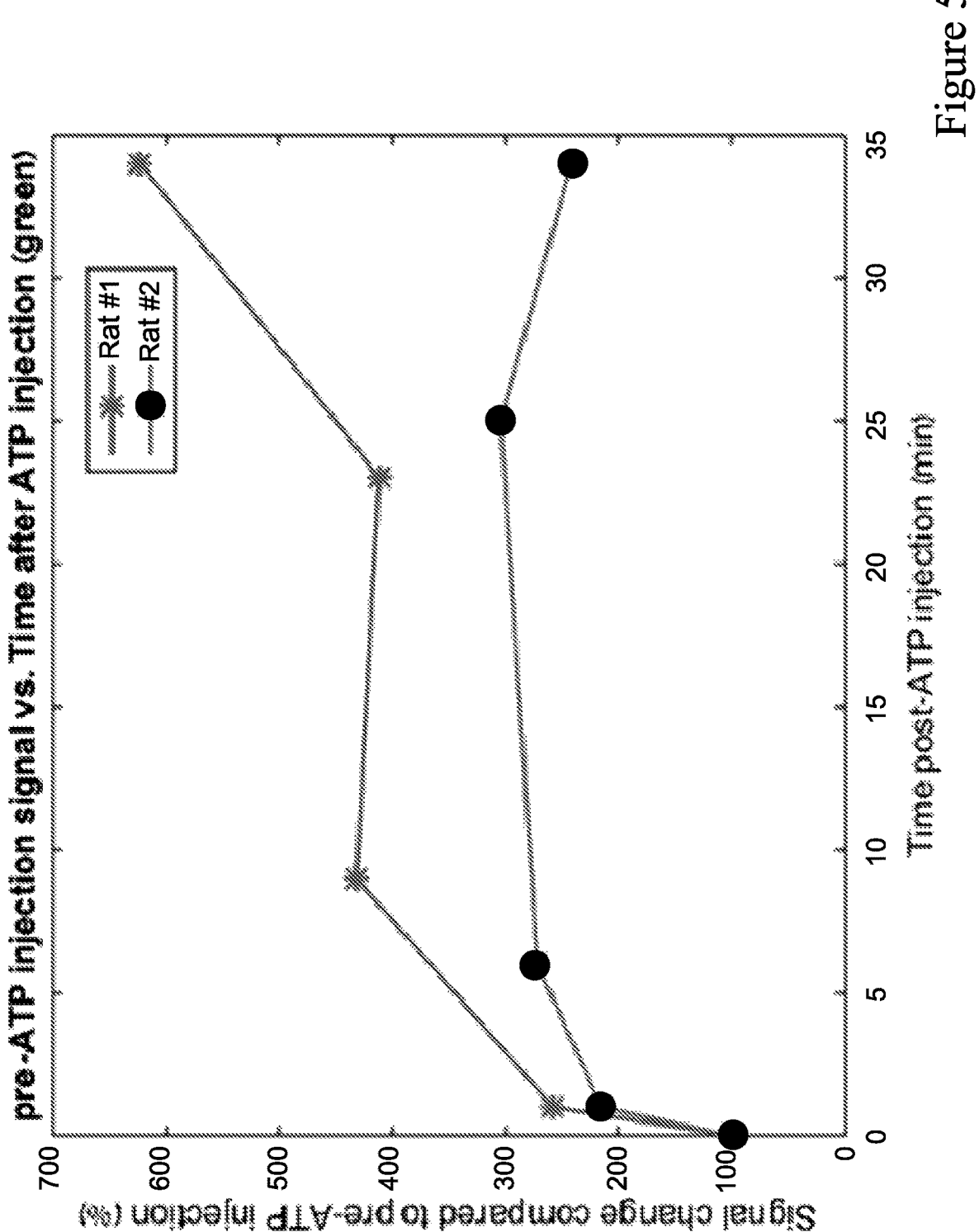
FIG. 5 shows sensing capabilities of the C-dot aptamer by fluorescence measurement after ATP injection.

Results: Absorbance for the three cell types for different concentrations is presented in FIG. 4. Cells viability was not affected even at the highest C-dot concentration.

EXAMPLE 4

In Vivo Toxicity

Methods: 5 Wistar male rats were taken for this experiment. Treatment for treated eyes (n=5) was done by topical administration of c-dot solution (3 mg/ml) for 15 minutes a day for 5 days. Eyes in the control group (n=5) same as treated eyes but with saline instead of c-dot solution. After treatment session, all eyes went through a test for SPKs (Superficial Punctate Keratitis) and Electroretinography measurements. Electroretinography measurements were done for each eye in two intensities (12.5 cd·s/m$^2$ and 50 cd·s/m$^2$)

Figure 6:
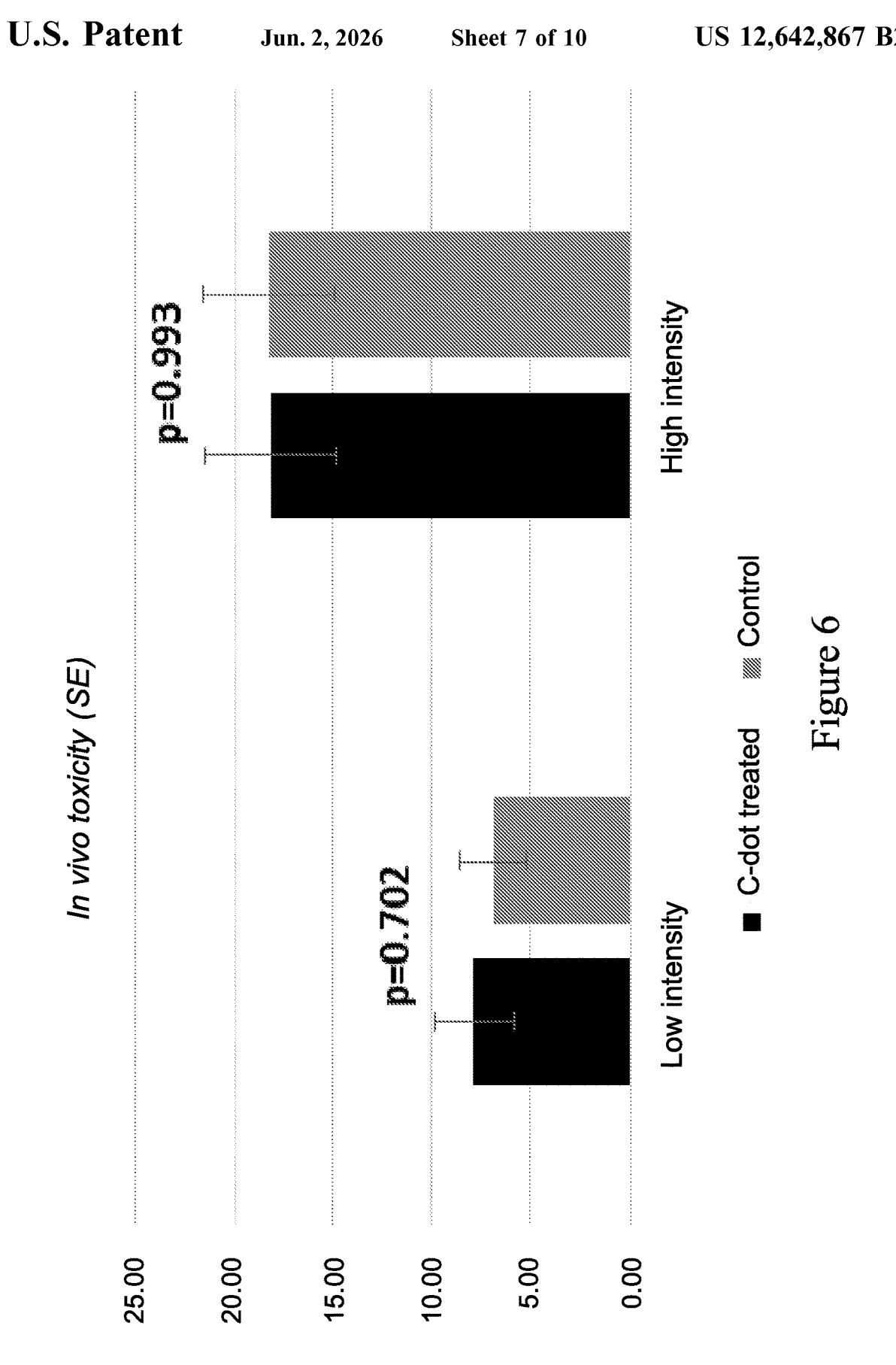
FIG. 6 shows no evidence for in vivo toxicity as measured by ERG electroretinography test, as presented in Example 4.

Results: No difference is SPKs was observed between treated and control groups, suggesting no corneal toxicity of the aptamer. Results of the ERG test were presented in FIG. 6 suggesting no retinal toxicity of the compound.

EXAMPLE 6

Ex Vivo Penetrability

Methods: Porcine eyes were taken for one hour of topical administration of c-dot solution (3 mg/ml). Aqueous humor, vitreous humor, lens and cornea were extracted from each eye. Extraction was done in several period of the after topical administration: 0 hrs (n=4), 1 hrs (n=4) and 4 hrs (n=5). Eyes in the control group were topically administrated with saline instead c-dot solution. Fluorescence readout of the extraction was done by a plate reader (excitation at A=420 nm, measurement at A=520 nm).

Figure 7:
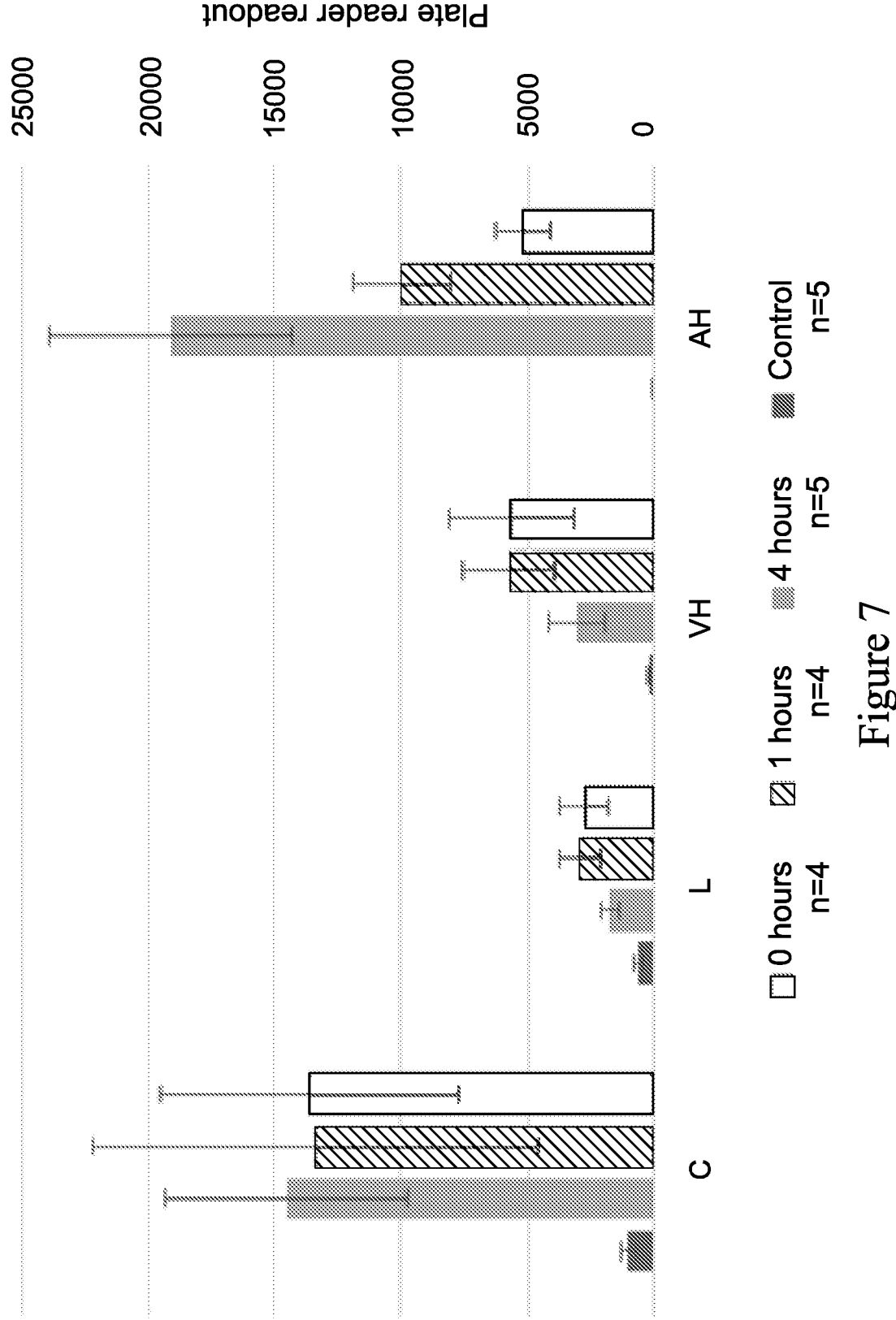
FIG. 7 shows the plate reader readout of the extraction.

Results: Plate reader readout of the extraction is shown in FIG. 7. C-dots shows good penetrability to the aqueous humor.

EXAMPLE 7

In Vitro No Aptamer Complementary C-Dot Testing

Methods: C-dot with quencher were synthesized in a new method without the use of aptamer complementary segment. To types were prepared—ATP sensitive C-dots and Cocaine sensitive C-dots. ATP/Cocaine solution at different concentrations was added. Fluorescence spectra (excitation at 470 nm) was measured two hours after ATP/Cocaine was added.

Figure 8:
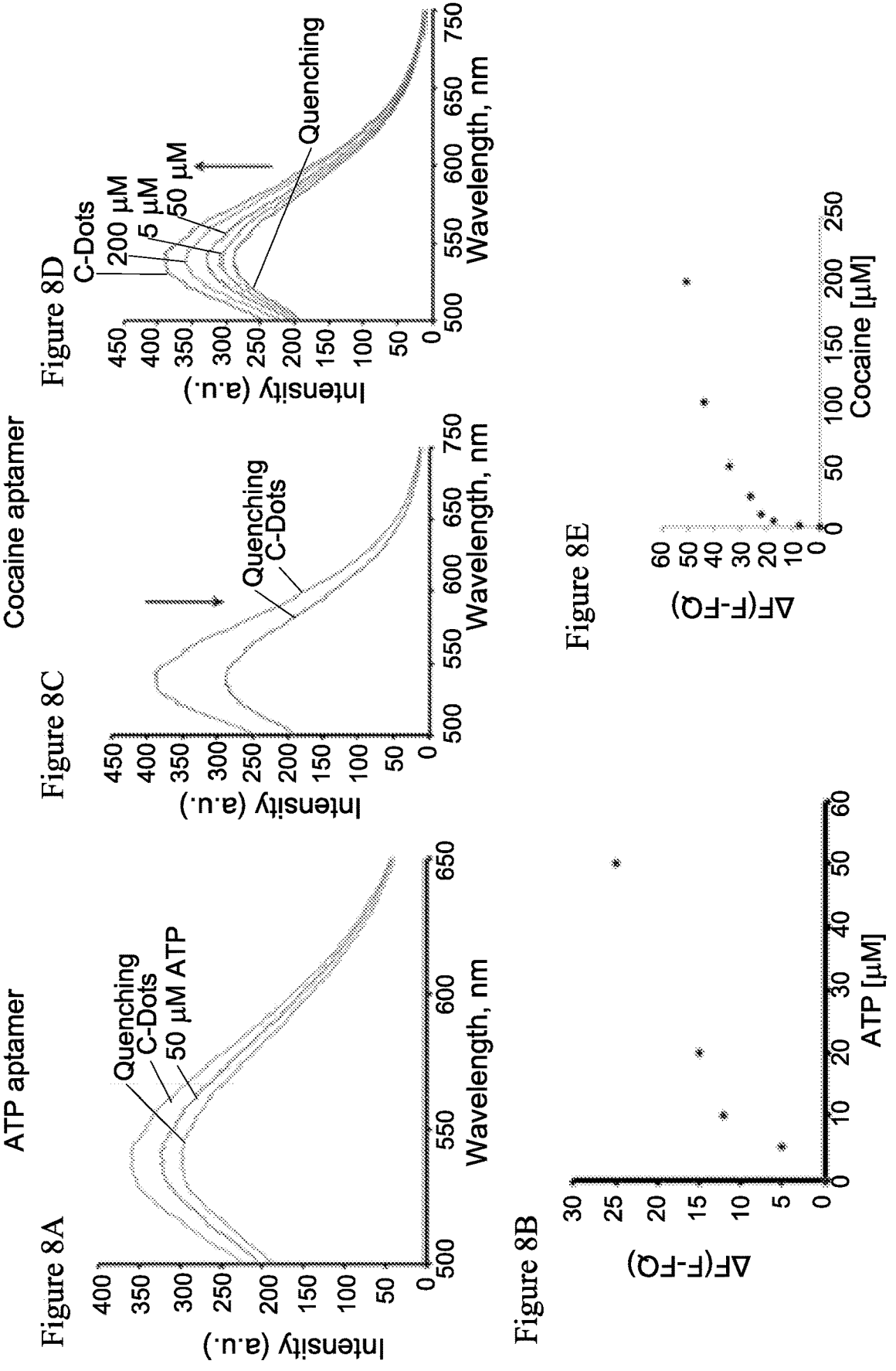
FIGS. 8A-8E show the fluorescence spectra for raw, quenched and post ATP/Cocaine.

Results: Fluorescence spectra for raw, quenched and post ATP/Cocaine is shown in FIG. 8. Fluorescence change versus ATP/Cocaine is also shown.

EXAMPLE 8

Establishment of C-Dot Synthesis Procedure

Synthesis route towards water-soluble luminescent C-dots: First, citric acid (3 g) and urea (3 g) were added to distilled water (10 mL) to form a transparent solution. The solution was then heated in a domestic 750 W microwave oven for 4-5 mins, during which the solution changed from being a colorless liquid to a brown and finally dark-brown clustered solid, indicating the formation of C-dots. This solid was then transferred to a vacuum oven and heated at 60° C. for 1 hour to remove the residual small molecules. An aqueous solution of the C-dots was purified in a centrifuge (3000 r·min$^{-1}$, 20 min) to remove large or agglomerated particles. The resulting colored (brown) aqueous solution remained indefinitely stable at various concentrations. The dilute aqueous solution of the C-dots exhibits excitation-wavelength-dependent photoluminescence properties with emission peaks ranging from 440 nm (blue) to 570 nm (yellow) at excitation from 340 nm to 500 nm. The strongest fluorescence emission band, located at 540 nm, is observed under 470 nm excitation.

Fluorescence Quenching and Detection of ATP: Adsorption of a quencher labeled aptamer against ATP (SEQ ID NO: 3) onto the C-dots, leading to the fluorescence quenching of the C-dots. For the detection of ATP, 10 μL of SEQ. ID. 1, 100 μM, was first added to 100 μL HEPES buffer solution, 20 mM, pH=7.4, 50 mM NaCl, that included 0.03 mg C-dots. Then, the C-dots solution with the aptamer was cleaned by sucrose solution, 3M, to remove access of aptamer. Then, different concentrations of ATP were added to the C-dots solution and left for different time-intervals at room temperature, after which, fluorescence of the mixture was measured.

```
                                        (SEQ ID NO: 3)
5'-ACC TGG GGG AGT ATT GCG GAG GAA GGT T/FQ/-3'
```

EXAMPLE 9

Preparation of C-Dot=V7t1 Complex

All nucleic acid strands were provided by Integrated DNA Technologies Inc. (Coralville, IA). The detailed DNA sequences used in the present study are:

```
Cap-VEGF
                                        (SEQ ID NO: 2)
5'-NH₂-(CH₂)₆-TCTACCCGGCCC-3'

Anti-VEGF aptamer
                                        (SEQ ID NO: 4)
5'-TGTGGGGGTGGACGGGCCGGGTAGA-3'.
```

Synthesis of C-dots. Citric acid and urea were mixed in water and heated for 4-5 min in a domestic 750 W microwave. An aqueous solution of the C-dots was purified in a centrifuge (14000 rpm for 20 min) to remove large agglomerated particles. The resulting solution was further purified from large particles using a microcon (Millipore) spin filter unit (MWCO 10 kDa).

Synthesis of succinic anhydride-functionalized carbon dots (SA-C-dots): First, 25 mg of C-dots were dispersed in 5 mL of water and the pH was adjusted to 7.0 with NaOH. Subsequently, 500 mg of succinic anhydride was added to the C-dots solution, followed by stirring overnight at 60° C. and then, 1254, of 2 Molar NaCl solution and 45 mL of ethanol were added to the reaction solution. The resulting SA-C-dots were collected by centrifugation (14000 rmp for 5 min) and washed using 50 mM NaCl solution and 90% ethanol for two times. The product was dried under vacuum at room temperature.

Preparation of cap-VEGF(1)/anti-VEGF aptamer (SEQ ID NO 4)-functionalized C-dots. Firstly, 0.5 mg of SA-C-dots were dispersed in 200 μL of MES buffer (2.5 mM, pH=5.5) and bubbled with argon for 15 min 13.37 mg of N-(3-Dimethylaminopropyl)-N'-ethylcarbodiimide hydrochloride (EDC) and 8.05 mg of N-Hydroxysulfosuccinimide sodium salt (NHS) were added to the reaction solution, and mixed for 15 min. And then, 200 μL of 1 mM cap-VEGF (SEQ ID NO 2) in PB buffer (0.2 M, pH=7.4) was added to the reaction solution. After an overnight incubation under room temperature, 3.6 mL of ethanol was added, and the mixture was set for a few minutes and then centrifuged at 14 000 rpm for 5 min. The resulting functionalized C-dots (functionalized with SEQ ID NO 2 were subjected to two rinsing steps: (1) 0.4 mL of 50 mM NaCl solution and 3.6 mL of ethanol and (2) 0.4 mL of HEPES buffer (10 mM, 150 mM NaCl, pH=7.2) and 3.6 mL of ethanol. The product was collected by centrifugation (14000 rmp for 5 min) and dried under vacuum at room temperature for 2 h. The loading of functionalized C-dots was determined by UV-Vis spectrophotometry.

To prepare aptamer associated product with the functionalized C-dots, 0.07 μmol anti-VEGF aptamer (SEQ ID NO 4) was added to 200 μL of 0.35 mg/mL functionalized C-dots in HEPES buffer (10 mM, 150 mM NaCl, pH=7.2), heated at 95° C. for 5 min and incubated overnight under 37° C. Then, 200 μL of the reaction solution was mixed with 1.8 mL of ethanol under 4° C. and centrifuged (14000 rpm, 5 min). The product was dried under vacuum at room temperature. The loading of C-dots with the aptamer sequence was determined by UV-Vis spectrophotometry.

EXAMPLE 10

Preparation of VEGF Sensitive MOFs

The detailed DNA sequences used in the present study are:

```
Binding aptamer
                                        (SEQ ID NO 2)
5'-NH₂-(CH₂)₆-TCTACCCGGCCC-3'

VEGF aptamer (2)
                                        (SEQ ID NO 4)
5'-TGTGGGGGTGGACGGGCCGGGTAGA-3'
```

Synthesis of azide-functionalized NMOFs (NMOF-N₃): First, the organic ligand, amino-triphenyl dicarboxylic acid (amino-TPDC), was synthesized according to He et al. 2014. Afterwards, NMOFs were prepared by heating ZrCl₄ with amino-TPDC at 80° C. for 5 days. The resulting NMOFs were collected by centrifugation and washed with DMF, triethylamine/ethanol (1:20, V/V), and ethanol gradually. For the preparation of azide modified NMOFs (NMOF-N₃), 10 mg of the dried NMOFs were dispersed in 3 mL of THF, followed by adding 1.0 mL of the tert-butyl nitrite (tBuONO) and 0.9 mL of the azidotrimethylsilane (TMSN3). And then, the reaction mixture was stirred at the room temperature overnight to obtain NMOF-N₃.

Synthesis of nucleic acid functionalized NMOFs: NMOF-N3 (10 mg, 2 mL) were added to an aqueous solution of DBCO-modified nucleic acid (1) (200 nmol, 1 mL). The mixture was incubated at 40° C. for 72 h, and three portions of a NaCl solution were added to the reaction mixture every two hours within the first 6 hours to reach a final concentration of 0.5 M. Thereafter, the obtained nucleic acid (1)-functionalized NMOFs were washed three times with HEPES buffer (10 mM, pH=7.4) to remove unbound DNA. The UV absorbance of the wash was measured at 260 nm to evaluate the amount of DNA loading on the NMOFs.

Loading of nucleic acid functionalized NMOFs: The nucleic acid functionalized NMOFs, 5 mg, were incubated with Rhodamine 6G (0.5 mg/mL) overnight in 2 mL of HEPES buffer solution (10 mM, pH=7.4). Subsequently, the NMOFs were separated and transferred to a HEPES buffer solution (10 mM, pH=7.4) that contained NaCl, 20 mM, and NMOFs were hybridized with the nucleic acid (2), leading to the locked state of the duplex DNA-functionalized NMOFs loaded with Rhodamine 6G. After 12 h, the resultant NMOFs were washed several times to remove the excess and nonspecifically bound Rhodamine 6G.

VEGF-induced unlocking of the NMOFs and the release of the encapsulated loads: Experiments were performed using solutions of the respective Rhodamine 6G-loaded aptamer-functionalized-locked NMOFs at a concentration corresponding to 1 mg/mL. Then, the NMOFs solutions, 30 μL, were treated with 10 μL of variable concentrations of VEGF for a fixed time-interval of 30 minutes. Other proteins, e.g. thrombin, hemoglobin, BSA, were used as controls to demonstrate the selective uncapping of the NMOFs by VEGF. After incubation, the respective samples were centrifuged at 10000 rpm for 10 min to precipitate the NMOFs, and the fluorescence of the released loads in the supernatant solution was measured using a Cary Eclipse Fluorescence Spectrophotometer.

Synthesis of Carbon dots (C-dots). The C-dots were synthesized according to Wang et Al. (ref1) Citric acid and urea were mixed in water and heated at 750 W for 4-5 min in a domestic microwave. An aqueous solution of the C-dots was purified in a centrifuge (14000 rpm, 20 min) to remove large agglomerated particles. The resulting solution was further purified from larger particles using microtron (Millipore) spin filter unit (MWCO 10 kDa).

Synthesis of succinic anhydride-functionalized Carbon dots (SA-C-dots): 25 mg of C-dots (1) were dispersed in 5 mL of water and the pH was adjusted to 7.0 with concentrated NaOH. Subsequently, 0.5 g of succinic anhydride was added to the C-dots solution, followed by stirring overnight at 60 C. The C-dots were washed 3 times from unreacted succinic anhydride by centrifugation in 90% v/v Ethanol and 10% v/v aqueous 50 mM NaCl (14000 rpm, 5 min) and dried under vacuum at room temperature.

Preparation of cap-VEGF/anti-VEGF aptamer-functionalized C-dots: Firstly, 0.5 mg of SA-C-dots were dispersed in 200 uL of MES buffer (2.5 mM, pH 5.5) and bubbled with argon for 15 min 13.37 mg of N-(3-Dimethylaminopropyl)-N'-ethylcarbodiimide hydrochloride (EDC) and 8.05 mg of N-Hydroxysulfosuccinimide sodium salt (NHS) were added to the reaction solution, and mixed for 15 min. 200 uL of 1 mM cap-VEGF in PB buffer (0.2 M, pH 7.4) was added to the reaction solution. After overnight incubation at room temperature, 3.6 mL of ethanol was added, the mixture was set for a few minutes and centrifuged at 14000 rpm for 5 min. The resulting (1)-functionalized C-dots were subjected to two rinsing steps: (1) 0.4 mL of 50 mM NaCl solution and 3.6 mL of ethanol and (2) 0.4 mL of HEPES buffer (10 mM, 150 mM NaCl, pH 7.2) an 3.6 mL of ethanol. The product was collected by centrifugation (14000 rpm for 5 min) and dried under vacuum at room temperature for 2 hours. The loading of C-dots with (2) was determined by UV-Vis spectrophotometry.

EXAMPLE 11

In Vivo Dynamics

Methods: Fluorescence was measured for 120 minutes after c-dot administration was completed. Concentration was calculated and normalized to t=0 min concentration.

Results: C-dot concentration half time was about 20 minutes.

EXAMPLE 12

In Vivo Penetration

Methods: C-dot solution (3 mg/ml) was topically administrated for 14 eyes. Seven eyes were administrated for 60 minutes while seven other eyes were administrated for five minutes. Saline solution was administrated for 60 minutes for six eyes as control. Fluorescence was measured right after administration and c-dot concentration was calculated based on our calibration experiments.

Results: Mean c-dot concentration was 15 μg/ml for five minutes administration and 60 μg/ml for 60 minutes administration.

EXAMPLE 13

Treatment—In Vitro Model (1)

Methods: Rat's eyes were enucleated; the choroid layer was separated from the retina, cut into approximately ~2 mm pieces and seeded in matrigel, with medium and different concentrations of VEGF. The cultures were monitored for blood vessel formation for 8 days.

Results: Sprouting growth tends to increase as VEGF concentration increases. This is validating our model for the following VEGF inhibition experiments.

EXAMPLE 14

Treatment—In Vitro Model (2)

Methods: Rat's eyes were enucleated; the choroid layer was separated from the retina, cut into approximately ~2 mm pieces and seeded in matrigel, with medium containing either common anti-VEGF agents, c-dot=aptamer complex, aptamer only and c-dot only. 2.6 nM VEGF were added to all samples. The cultures were monitored for blood vessel formation for 8 days.

Results: A similar effect was observed between common anti-VEGF agents and V7t1 aptamer with c-dot aptamer complex showing only slightly lesser effect.

EXAMPLE 15

Treatment—In Vitro Model (3)

Methods: Rat's eyes were enucleated; the choroid layer was separated from the retina, cut into approximately ~2 mm pieces and seeded in matrigel, with medium containing c-dot=aptamer complex in different concentrations. 2.6 nM VEGF were added to all samples. The cultures were monitored for blood vessel formation for 8 days.

Results: The results support the trend for which sprouting growth decreases as c-dot=aptamer complex concentration increases.

EXAMPLE 16

MOFs In Vivo Sensing

Methods: 5 µL sensitive VEGF MOFs (1 mg/ml), were injected to four eyes with Rhodamine 6G fluorescence measured for 30 minutes after injection. Then, 5 µL (10 µM) of VEGF were injected to three of those eyes and no injection of one eye. Rhodamine 6G was measured for 60 minutes.

Results: For the three VEGF injected eyes, elevation of the fluorescence signal in observed for the first 15 minutes. The fluorescence signal seems to decay through 60 minutes after VEGF injection. For the no injection eye, the fluorescence signal is stable for the entire measurement session.

The invention claimed is:

1. A method of treating an ophthalmic disease or disorder associated with ocular angiogenesis in a subject, selected from macular degeneration, age related macular degeneration, wet macular degeneration, dry macular degeneration and diabetic retinopathy, the method comprising:

topically administering to an eye of a subject having said ophthalmic disease or disorder an antiangiogenic agent comprising a carbon quantum dot (C-dot) having a plurality of nucleic acids associated therewith, each nucleic acid in said plurality of nucleic acids having a sequence comprising at least 9 nucleic acid bases hybridized to at least 9 nucleic acid bases of a complementary nucleic acid sequence comprised within a sequence of at least one ocular angiogenesis growth factor (OAGF) aptamer, wherein said antiangiogenic agent penetrates the eye cornea and said hybridization dissociates upon binding of at least one ocular angiogenesis growth factor in the eye to said at least one aptamer.

---

SEQUENCE LISTING

<160> NUMBER OF SEQ ID NOS: 4

<210> SEQ ID NO 1
<211> LENGTH: 12
<212> TYPE: DNA
<213> ORGANISM: Artificial Sequence
<220> FEATURE:
<223> OTHER INFORMATION: single-stranded DNA sequences

<400> SEQUENCE: 1
tctacccggc cc                                                    12

<210> SEQ ID NO 2
<211> LENGTH: 12
<212> TYPE: DNA
<213> ORGANISM: Artificial Sequence
<220> FEATURE:
<223> OTHER INFORMATION: the sequences segment associated with the
      vehicle surface having the sequence 5'-NH2-(CH2)6-TCTACCCGGCCC-3'.

<400> SEQUENCE: 2
tctacccggc cc                                                    12

<210> SEQ ID NO 3
<211> LENGTH: 28
<212> TYPE: DNA
<213> ORGANISM: Artificial Sequence
<220> FEATURE:
<223> OTHER INFORMATION: sequences segment of anti-VEGF aptamer

<400> SEQUENCE: 3
acctggggga gtattgcgga ggaaggtt                                   28

<210> SEQ ID NO 4
<211> LENGTH: 25
<212> TYPE: DNA
<213> ORGANISM: Artificial Sequence
<220> FEATURE:
<223> OTHER INFORMATION: sequences segment of VEGF aptamer

<400> SEQUENCE: 4
tgtgggggtg gacgggccgg gtaga                                      25

2. The method according to claim 1, wherein the C-dot is surface associated with each of the nucleic acids via non-covalent interaction.

3. The method according to claim 1, wherein the C-dot is functionalized with amine or carboxylic groups which associate to the plurality of nucleic acids.

4. The method according to claim 1, wherein the C-dot is surface-associated with each of the nucleic acids via a covalent bond or the C-dot is surface associated with each of the nucleic acids via non-covalent interaction or the C-dot is functionalized with amine or carboxylic groups which associate to the plurality of nucleic acids.

5. The method according to claim 1, wherein at least a portion of the plurality of nucleic acids associated with the C-dot are single-stranded DNA having a sequence consisting of or comprising 5'-TCTACCCGGCCC-3' (SEQ ID NO: 1).

6. The method according to claim 5, wherein the single-stranded DNA has the structure 5'-NH$_2$—(CH$_2$)$_n$-TC-TACCCGGCCC-3' (SEQ ID NO:2), wherein n is an integer between 1 and 10.

7. The method according to claim 6, wherein the C-dot is surface-associated with a plurality of single-stranded DNA sequences of SEQ ID NO:2, wherein n is 2 or 6.

8. The method according to claim 1, wherein the C-dot is associated with a plurality of sequences having 5'-NH$_2$—(CH$_2$)$_6$-TCTACCCGGCCC-3' (SEQ ID NO:2), wherein n is 6, each of the plurality of sequences being hybridized to the aptamer.

9. The method according to claim 1, wherein the aptamer is of a sequence selected from the group consisting of:

```
                                        (SEQ ID NO: 3)
5'-ACCTGGGGGAGTATTGCGGAGGAAGGTT-3',
and (SEQ ID NO: 4)
5-TGTGGGGGTGGACGGGCCGGGTAGA-3'.
```

10. The method according to claim 1, wherein the C-dot is surface-associated with each of said nucleic acids via a covalent bond.

* * * * *